US008765169B2

(12) United States Patent
Kemp et al.

(10) Patent No.: US 8,765,169 B2
(45) Date of Patent: Jul. 1, 2014

(54) WOUND HEALING PROFILE

(75) Inventors: Paul Kemp, Romiley (GB); Györgyi Talas, Timperley (GB); Jennifer Sutherland, Stockport (GB); Margaret Batten, Whiston (GB); Penelope Ann Johnson, Glossop (GB); Andrew Shering, Chorlton (GB); Michael McWhan, Glossop (GB)

(73) Assignee: Smith & Nephew, Inc., Memphis, TN (US)

( * ) Notice: Subject to any disclaimer, the term of this patent is extended or adjusted under 35 U.S.C. 154(b) by 1579 days.

(21) Appl. No.: 10/589,150

(22) PCT Filed: Feb. 14, 2005

(86) PCT No.: PCT/GB2005/000511
§ 371 (c)(1),
(2), (4) Date: Jul. 2, 2007

(87) PCT Pub. No.: WO2005/079821
PCT Pub. Date: Sep. 1, 2005

(65) Prior Publication Data
US 2008/0193507 A1    Aug. 14, 2008

Related U.S. Application Data

(60) Provisional application No. 60/556,194, filed on Mar. 25, 2004, provisional application No. 60/556,155, filed on Mar. 25, 2004, provisional application No. 60/632,425, filed on Dec. 1, 2004.

(30) Foreign Application Priority Data

Feb. 13, 2004 (GB) .................................. 0403220.7
Feb. 13, 2004 (GB) .................................. 0403226.4
Nov. 30, 2004 (GB) .................................. 0426252.3

(51) Int. Cl.
 *A61F 13/00* (2006.01)
 *A61K 9/70* (2006.01)
 *C12N 5/071* (2010.01)
 *C12N 5/00* (2006.01)
 *C12N 5/02* (2006.01)

(52) U.S. Cl.
 USPC ........................................................ 424/443

(58) Field of Classification Search
 None
 See application file for complete search history.

(56) References Cited

U.S. PATENT DOCUMENTS

| | | | |
|---|---|---|---|
| 5,591,444 | A | 1/1997 | Boss, Jr. |
| 5,858,390 | A | 1/1999 | Boss, Jr. |
| 6,124,522 | A | 9/2000 | Schroeder |
| 6,533,819 | B1 | 3/2003 | Urry et al. |
| 6,699,470 | B1 | 3/2004 | Ameer et al. |
| 6,878,383 | B2 | 4/2005 | Boss, Jr. et al. |
| 2002/0161440 | A1 | 10/2002 | Son et al. |
| 2003/0069639 | A1 | 4/2003 | Sander et al. |
| 2003/0165482 | A1 | 9/2003 | Rolland et al. |
| 2004/0029095 | A1 | 2/2004 | Lowel et al. |
| 2004/0082063 | A1 | 4/2004 | Deshpande et al. |
| 2004/0162615 | A1 | 8/2004 | Lam et al. |

FOREIGN PATENT DOCUMENTS

| | | |
|---|---|---|
| CA | 2556098 | 9/2005 |
| DE | 10116362 | 10/2002 |
| EP | 0 242 305 | 10/1987 |
| EP | 0 344 924 | 12/1989 |
| EP | 1 184 040 | 3/2002 |
| EP | 0 989 866 | 9/2002 |
| EP | 1358857 | 11/2003 |
| EP | 1 375 647 | 1/2004 |
| EP | 1 137 380 | 3/2004 |
| RU | 2023424 | 11/1994 |
| RU | 2195889 | 1/2003 |
| RU | 2273457 | 4/2006 |
| WO | WO 98/36704 | 8/1998 |
| WO | WO99/15637 | 4/1999 |
| WO | WO 99/51164 | 10/1999 |
| WO | WO 01/32129 | 5/2001 |
| WO | WO02/072113 | 9/2002 |
| WO | WO03/041568 | 5/2003 |
| WO | WO 03/084385 | 10/2003 |

OTHER PUBLICATIONS

Berfield et al., "Insulin-like Growth Factor I (IGF-I) Induces Unique Effects in the Cytoskeleton of Cultured Rat Glomerular Mesangial Cells," *The Journal of Histochemistry & Cytochemistry* 45: 583-593, 1997.
Brown et al., "Fibroblast Migration in Fibrin Gel Matrices," *American Journal of Pathology* 142: 273-283, 1993.
Clark, "Regulation of Fibroplasia in Cutaneous Wound Repair," *The American Journal of the Medical Sciences* 306: 42-48, 1993.
Cullen et al., "The Differential Regulation and Secretion of Proteinases from Fetal and Neonatal Fibroblasts by Growth Factors," *Int. J. Biochem. Cell Biol.* 29: 241-250, 1997.
Eckes et al., "Impaired Wound Healing in Embryonic and Adult Mice Lacking Vimentin," *Journal of Cell Science* 113: 2455-2462, 2000.
Kessler et al., "Fibroblasts in Mechanically Stressed Collagen Lattices Assume a 'Synthetic' Phenotype," *The Journal of Biological Chemistry* 276: 36575-36585, 2001.
Kessler-Becker et al., "Expression of Pro-Inflammatory Markers by Human Dermal Fibroblasts in a Three-Dimensional Culture Model is Mediated by an Autocrine Interleukin-1 Loop," *The Biochemical Journal* 379: 351-358, 2004.

(Continued)

*Primary Examiner* — Valarie Bertoglio
(74) *Attorney, Agent, or Firm* — Fulbright & Jaworski LLP

(57) ABSTRACT

The present invention relates to compositions and methods for tissue regeneration, particularly for treating skin lesions such as wounds. In one aspect, the invention provides wound healing composition characterized by the higher expression levels of phenotypic marker genes such as apolipoprotein D, matrix metalloprotease (2), collagen 3a1 and smooth muscle actin than the housekeeping gene ribosomal protein L32. The compositions and methods of the invention are useful especially for assisting the process of wound healing, particularly chronic open lesions that are slow to heal or resistant to healing.

21 Claims, 9 Drawing Sheets

(56) References Cited

OTHER PUBLICATIONS

Figure 1:
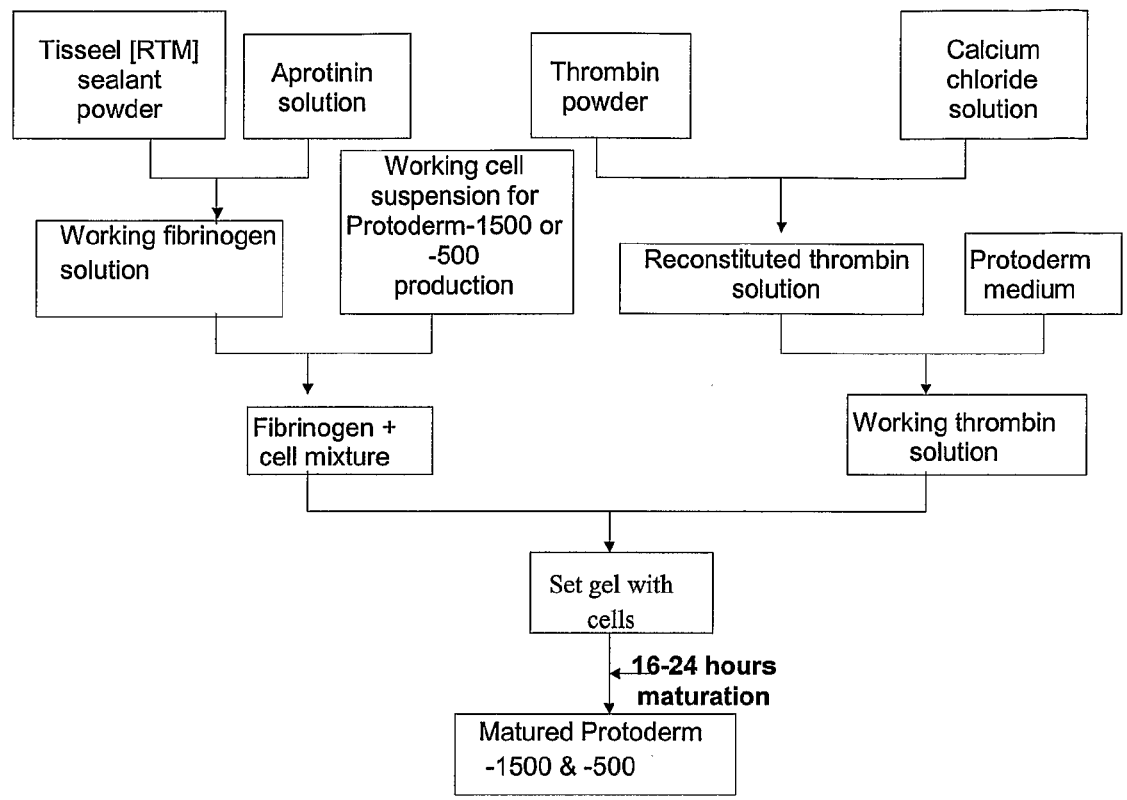

Meana et al., "Large Surface of Cultured Human Epithelium Obtained on a Dermal Matrix Based on Live Fibroblast-Containing Fibrin Gels," *Burns* 24: 621-630, 1998.

Muhart et al., "Behavior of Tissue-Engineered Skin: A Comparison of a Living Skin Equivalent, Autograft, and Occlusive Dressing in Human Donor Sites," *Arch. Dermatol.* 135: 913-918, 1999.

Neidert et al., "Fibrin as an Alternative Biopolymer to Type I Collagen for Tissue-Equivalent Fabrication," *Proceedings of the 2001 Bioengineering Conference* 50: 215-216, 2001.

Schäffer et al., "Nitric Oxide, an Autocrine Regulator of Wound Fibroblast Synthetic Function," *The Journal of Immunology* 158: 2357-2381, 1997.

Tuan et al., "In Vitro Fibroplasia: Matrix Contraction, Cell Growth, and Collagen Production of Fibroblasts Cultured in Fibrin Gels," *Experimental Cell Research* 223: 127-134, 1996.

Whiteside et al., "Heterogeneous Synthetic Phenotype of Cloned Scleroderma Fibroblasts May be Due to Aberrant Regulation in the Synthesis of Connective Tissues," *Arthritis and Rheumatism* 31: 1221-1229, 1988.

Geesin et al., "Regulation of Collagen Synthesis in Human Dermal Fibroblasts in Contracted Collagen Gels by Ascorbic Acid, Growth Factors, and Inhibitors of Lipid Peroxidation," *Exp. Cell Res.* 206:283-290, 1993.

Hansbrough et al., "Composite Grafts of Human Keratinocytes Grown on a Polyglactin Mesh-Cultured Fibroblast Dermal Substitute Function as a Bilayer Skin Replacement in Full-Thickness Wounds on Athymic Mice," *J. Burn Care & Rehab.* 14:485-494, 1993.

Neidert et al., "Enhanced Fibrin Remodeling In Vitro with TGF-β1, Insulin and Plasmin for Improved Tissue-Equivalents," *Biomaterials* 23:3717-3731, 2002.

Office Communication, issued in Canadian Patent Application No. 2,555,233, dated Jul. 6, 2011.

A
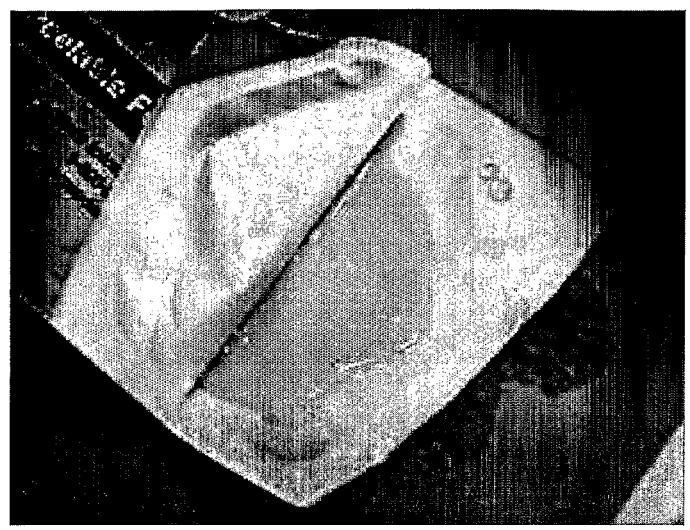
B
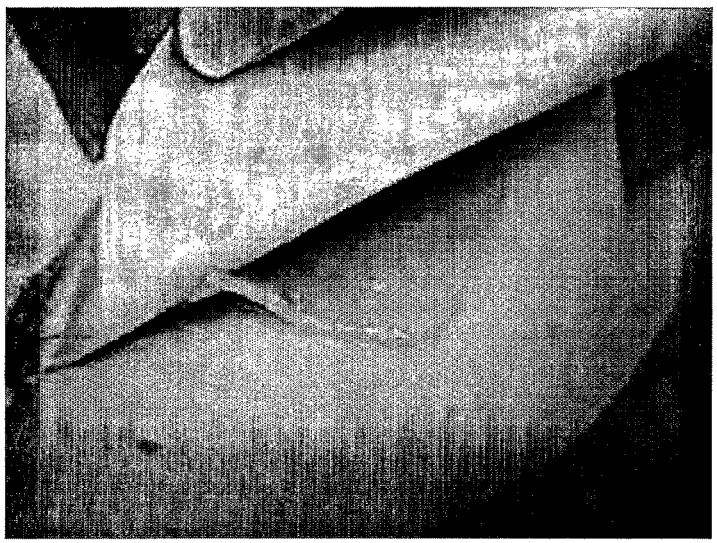
C
Fig. 2

WOUND HEALING PROFILE

CROSS-REFERENCE TO RELATED APPLICATIONS

This application is the U.S. National Stage of International Application No. PCT/GB2005/000511, filed Feb. 14, 2005, which claims benefit from Great Britain Application No. 0403220.7, filed Feb. 13, 2004, Great Britain Application No. 0403226.4, filed Feb. 13, 2004, U.S. Provisional Application No. 60/556,194, filed Mar. 25, 2004, U.S. Provisional Application No. 60/556,155, filed Mar. 25, 2004, Great Britain Application No. 0426252.3, filed Nov. 30, 2004, and U.S. Provisional Application No. 60/632,425, filed Dec. 1, 2004, each of which is hereby incorporated by reference.

The present invention relates to compositions and methods for tissue regeneration, particularly for treating skin lesions such as wounds. The compositions and methods are useful especially for assisting the process of wound healing, particularly chronic open lesions that are slow to heal or resistant to healing.

Healing of open wounds extending through the germinal epithelium in otherwise healthy tissue takes place by the process classically described as "second intention", which, following initial haemostasis, involves a well-ordered sequence of inflammation, cellular infiltration, angiogenesis, granulation and re-epithelialisation. As part of the normal healing response, resident fibroblasts are required to undergo a series of phenotypic changes, migrating to the wound site, then proliferating, then synthesising and secreting extracellular matrix molecules. In vivo, a least a proportion of fibroblasts then switch to a myofibroblastic phenotype in order to facilitate wound contraction.

In vitro, a series of phenotypically distinguishable mitotic and post-mitotic fibroblast populations have been described (Bayreuther et al., 1988, Proc Natl Acad Sci USA 85: 5112-5116). The pathway of differentiation appears to be controlled, at least in part, by interactions between fibroblasts and extracellular matrix (ECM) proteins present at the wound site. Growth factors and cytokines undoubtedly also exert an important influence, although their effects too, appear to be modulated by fibroblast exposure to particular ECM proteins. Among the ECM proteins that appear to have an important role in fibroblast differentiation are fibrinogen and fibrin. Fibroblasts specifically interact with fibrin and fibrinogen "RGD" motifs through $\alpha_v\beta_3$ integrin receptors although the cellular response is complex and modulated by other factors. In vitro studies of the effect of fibrin glue on human periodontal ligament fibroblasts have suggested that fibrin appeared to slightly inhibit fibroblast proliferation. The presence of a fibrin matrix has also been reported to increase the synthesis of collagen by entrapped fibroblasts (Neidert et al, 2001, Proceedings of the ASME Bioengineering Conference, Kamm et al. [Eds], Vol 50: 215-216).

Fibroblasts are also known to have a role in the remodelling of fibrin clots. As new extracellular matrix proteins such as collagen type I and III, fibronectin and vitronectin are laid down, the fibrin matrix is broken down, predominantly by the activation of the plasma-derived enzyme plasmin. This is regulated by the activation (or inhibition) of its proenzyme, plasminogen, by a variety of plasminogen activators and inhibitors. In vivo, a number of infiltrating cells, such as neutrophils and macrophages, secrete urokinase-type plasminogen activator (uPA), whilst endothelial cells are largely responsible for producing tissue plasminogen activator (tPA). Fibroblasts also secrete both uPA and plasminogen activator inhibitors, such as plasminogen activator inhibitor-1 (PA-1).

The balance between these antagonistic mediators is crucial in controlling fibrin remodelling and scar formation. The expression of the antagonistic mediators is developmentally regulated, as well as being controlled by extracellular matrix components and local growth factors.

To facilitate movement through a cross-linked fibrin clot and a tight meshwork of extracellular matrix, a variety of fibroblast- and serum-derived enzymes cleave a path for migration. These include interstitial collagenase (matrix metalloproteinase-1, MMP-1), gelatinase (matrix metalloproteinase-2, MMP-2), stromelysin (matrix metalloproteinase-3, MMP-3) and the plasminogen activators. Chemotactic factors such as TGF-β and PDGF may upregulate the production and secretion of these enzymes.

Once migrating fibroblasts reach a wound, they gradually become secretory and protein synthesis is increased. The previously retracted endoplasmic reticulum and Golgi apparatus becomes dispersed throughout the cytoplasm and a loose matrix is produced, which is mainly composed of fibronectin and type III collagen. Ultimately, this profibrotic phenotype takes over, which is characterised by an abundance of rough endoplasmic reticulum and Golgi apparatus, secreting newly synthesised collagen in response to highly expressed TGF-β. Notwithstanding, TGF-β fails to upregulate further collagen deposition, once a matrix has been deposited. It is also thought that IL-4 released by mast cells induces a modest increase in types I and III collagen together with fibronectin. Mast cells furthermore produce tryptase (a serine esterase) in abundance, which has been shown to upregulate fibroblast proliferation.

Stimuli such as TGF-α, TGF-β and PDGF responsible for fibroblast proliferation and matrix synthesis have been extensively investigated in vitro (Derynck, 1988, Cell 54: 593-595; Ross & Raines, 1990, In: Growth Factors: From genes to clinical applications, Sara et al. [Eds], pp. 193-199, Raven Press, New York; Sporn & Roberts, 1992, J Cell Biol 119: 1017-1021) and by in vivo manipulation of wounds (Sprugel et al., 1987, Am J Pathol 129: 601-613; Pierce et al., 1991, J Cell Biochem 45: 319-326). γ-interferon on the other hand was demonstrated to have a negative effect on the mitogenic and synthetic potential of fibroblasts in vitro and in vivo (Duncan & Berman, 1985, J Exp Med 162: 516-527; Granstein et al., 1987, J Clin Invest 79: 1254-1258). In addition, the collagen matrix itself can suppress these activities (Grinnell, 1994, J Cell Biol 124: 401-404; Clark et al., 1995, J Cell Sci 108: 1251-1261), whilst fibrin or fibronectin matrix have little or no suppressive effect (Clark et al., 1995, supra). Many fibroblasts undergo apoptosis (programmed cell death) in day-10 healing wounds, thereby marking the transition from a fibroblast-rich granulation tissue to a scar tissue with reduced cell density.

Where a wound has destroyed the germinal layer of epithelium, collagen deposition by infiltrating fibroblasts and re-epithelialisation results in a degree of scarring, with incomplete restoration of function in terms of the flexibility and elasticity of the original dermis and failure to regenerate auxiliary structures such as hair follicles and sweat glands.

A number of factors may adversely affect the rate and extent of such wound healing, in particular, poor blood supply. Poorly perfused tissue, often associated with impaired venous return and varicose veins, peripheral vascular disease or diabetes, often fails to heal satisfactorily, resulting in chronic ulcers, although the details of the pathogenesis are still unclear. Chronic leg ulcers in particular are a significant and growing problem world-wide.

Various approaches have been tried for the treatment of wounds. Autologous skin-grafting has been used to close open wounds, minimise the risk of opportunistic infection, accelerate healing and minimise scarring. Skin grafting has significant limitations, not least the requirement for a suitable donor site from which grafts can be taken which is a particular problem where wounds are extensive (for example, with burns). In addition, grafts have a low success rate where wound healing is compromised.

With respect to chronic leg ulcers in particular, the introduction of compression therapy in combination with moist wound dressings has been the standard therapeutic management.

More recently, tissue-engineering solutions have become available. Research into regenerative medicine has shown that human cells have substantial potential to heal and regenerate damaged tissue especially when primed by an environment that closely mimics the natural physiological condition being treated. Much of this research has focused on the production of so-called "tissue equivalents", which aim to provide a temporary functional replacement for missing tissue and accelerate healing. Tissue equivalents may be dermal equivalents or total skin equivalents, with the aim being to provide effective coverage of the wound as quickly as possible. The development and production of tissue equivalents usually involves the isolation of replacement skin cells, which are expanded and seeded onto or into a supporting structure such as a three-dimensional bio-resorbable matrix, or within a gel-based scaffold.

A variety of materials have been used as acellular protein matrices for wound healing applications. These include synthetic polyesters (polyglycolic acid (PGA), polylactic acid (PLA), polyglactide (Dermagraft®, Smith & Nephew, described below), polydioxanone, polyhydroxyalkonoates and hyaluronic acid derivatives), hydrophilic polyurethanes (polyetherpolyester, polyethylene oxide and carboxymethylcellulose ethylene), and collagen-based scaffolds (cross-linked elastin collagen material (Matriderm®), cross-linked collagens manufactured from acid-soluble type I bovine collagen material (such as Vitaphore®). An alternative approach is to use an acellular derivative of allogeneic human dermis, a natural dermal matrix from which cells have been removed (such as Alloderm®, LifeCell Corporation). Some preparations use an organised, layered structure in order to more closely mimic the structure and function of the dermis. For instance, a preparation comprising an underlying layer of bovine collagen and shark glycosaminoglycans with an overlying layer of silicone is known (Integra®, Integra LifeSciences Corporation).

Other approaches to wound healing have involved the use of fibrin sealants, for example Tisseel® (Baxter), Beriplast® (Aventis), Quixil® (Omrix Biopharmaceuticals), Haemaseel® (Haemacure) and Crosseal® (Omrix). These commercially available fibrin sealants are derived from cryoprecipitate of pooled plasma from virally-screened allogeneic donors.

Fibrin products rely on the natural polymerisation process that occurs during the physiological blood clotting cascade, in which a monomeric fibrin precursor, fibrinogen, is acted on by activated thrombin with the resultant production of polymeric fibrin. Fibrin forms the protein scaffold component of blood clots, to which platelets adhere.

Fibrin has been recognised as a convenient and clinically acceptable cell carrier to be used in tissue engineering applications. Commercially available products that utilise fibrin sealants for cell delivery include Bioseed® (Biotissue Technologies). The use of fibrin sealants for cell delivery purposes for the treatment burns has been suggested by several groups (see Brown et al., 1993, Am J Pathol 142: 273-283; Neidert et al., 2001, supra; Tuan et al., 1996, Exp Cell Res 223: 127-134; and US Patent Appl. No. 2003/01654482).

Exogenously applied dermal cells have been shown to have beneficial effects on wound healing including shorter time to complete healing (Falanga & Sabolinski, 1999, Wound Repair Regen 7: 210-207), delivery of active growth factors to the wound (Naughton et al., 1997, Artif Organs 21: 1203-1210), reduced potential for lesion recurrence (Gentzkow et al., 1996, Diabetes Care 19: 350-354), and reduced pain (Muhart et al., 1999, Arch Dermatiol 135: 913-918).

Known combinations of protein matrices and dermal cells for wound healing applications include a preparation called Dermagraft® (Smith & Nephew) comprising cryo-preserved primary human foreskin fibroblasts seeded onto a bioabsorbable glycolic-lactic acid polyester (polyglactide) scaffold (Naughton et al, 1997, supra; U.S. Pat. No. 4,963,489). The fibroblasts are allowed to proliferate in the scaffold, secreting extracellular matrix proteins and growth factors and cytokines. The mature preparation is packaged in 10% dimethylsulphoxide and bovine serum as a cryoprotectant to allow storage of the product by freezing prior to use. Disadvantages of this approach include difficulty in manipulating the product during application to the wound (such as ulcers), and the necessity of storing and transporting the product at very low temperatures ($-70°$ C.) and use of careful thawing procedures in order to ensure viability of the cells (see WO 87/06120).

Various combinations of collagen-based matrices and living cells are known. Apligraf® (Organogenesis, Inc.) is a bilayered structure comprising a lower ('dermal') layer of a bovine collagen scaffold supporting living human fibroblasts and an upper ('epidermal') layer comprising human keratinocytes on a collagen scaffold (Falanga & Sabolinski, 1999, supra; WO 99/63051). The preparation is supplied as a circular disk approximately 75 mm in diameter and 0.75 mm thick on an inert polycarbonate membrane. Apligraf® is packaged individually for use and has a 5-day shelf life. It is maintained in an agarose-rich nutrient with a 10% $CO_2$/air atmosphere and is shipped and stored at room temperature (20° C. to 31° C.; 68° F. to 88° F.). The removal of the product form the storage dish and polycarbonate membrane involves teasing away the edge of the Apligraf® using sterile forceps. Problems associated with this method include excessive folding which can make accurate, close application of the preparation to the wound difficult and time-consuming.

A similar product (Orcel®; Ortec International Inc) is described in U.S. Pat. No. 6,039,760. Orcel® is a bilayered structure of bovine collagen with fibroblasts and keratinocytes. The preparation is packaged between 2 non-adherent pieces of mesh, which are differently coloured to distinguish between sides. The device is then packaged in a plastic tray containing media to maintain cell viability during storage and shipping, which is further packaged into pouches with chill packs to maintain a temperature of 11° C. to 19° C. for 72 hours.

Another example of a tissue equivalent that attempts to reproduce a dermis-like arrangement of fibroblasts in a protein matrix supporting an overlying layer of keratinocytes is described in Meana et al. (1998, Burns 24: 621-630). Rama et al. (2001, Transplantation 72: 1478-1485) describe a method of culturing autologous limbal stem cells on a fibrin gel substrate for grafting to the contralateral cornea.

US Patent Appl. No. 20030165482 discloses a wound healing preparation (Allox®, Modex Therapeutiques SA) comprising growth-arrested allogeneic human fibroblasts and keratinocytes applied to a wound in a viscous paste of fibrinogen (Tisseel®) to which thrombin has been added, so that fibrinogen cleavage and fibrin polymerisation occur in situ.

Alternatively, the separate liquid components are sprayed onto the wound, to set in situ, on mixing.

The present invention provides an alternative wound healing preparation and associated products and methods which address problems associated with prior art products and methods.

According to a first aspect of the present invention there is provided a wound healing composition comprising isolated living cells having a wound healing phenotype, characterised in that the cells of the composition:
(i) exhibit a 2 to 48000-fold, more preferably a 100 to 2000-fold, higher level of expression of apolipoprotein D (ApoD) than of Ribosomal protein L32 (RPL32);
exhibit a 2000 to 1600000-fold, more preferably a 13000 to 100000-fold, higher level of expression of matrix metalloprotease 2 (MMP2) than of RPL32;
exhibit a 20 to 44000-fold, more preferably a 800 to 1800-fold, higher level of expression of collagen 3a1 (Col3a1) than of RPL32; and
exhibit a 20 to 150000-fold, more preferably a 1600 to 2500-fold, higher level of expression of smooth muscle actin (SMA) than of RPL32; and/or
(ii) have a banding pattern of polymerase chain reaction (PCR) products resulting from differential display identical or similar to that shown in FIG. 4 or FIG. 5 for nucleic acid expression in fibrin (for example, in a fibrin matrix).

Figure 4:
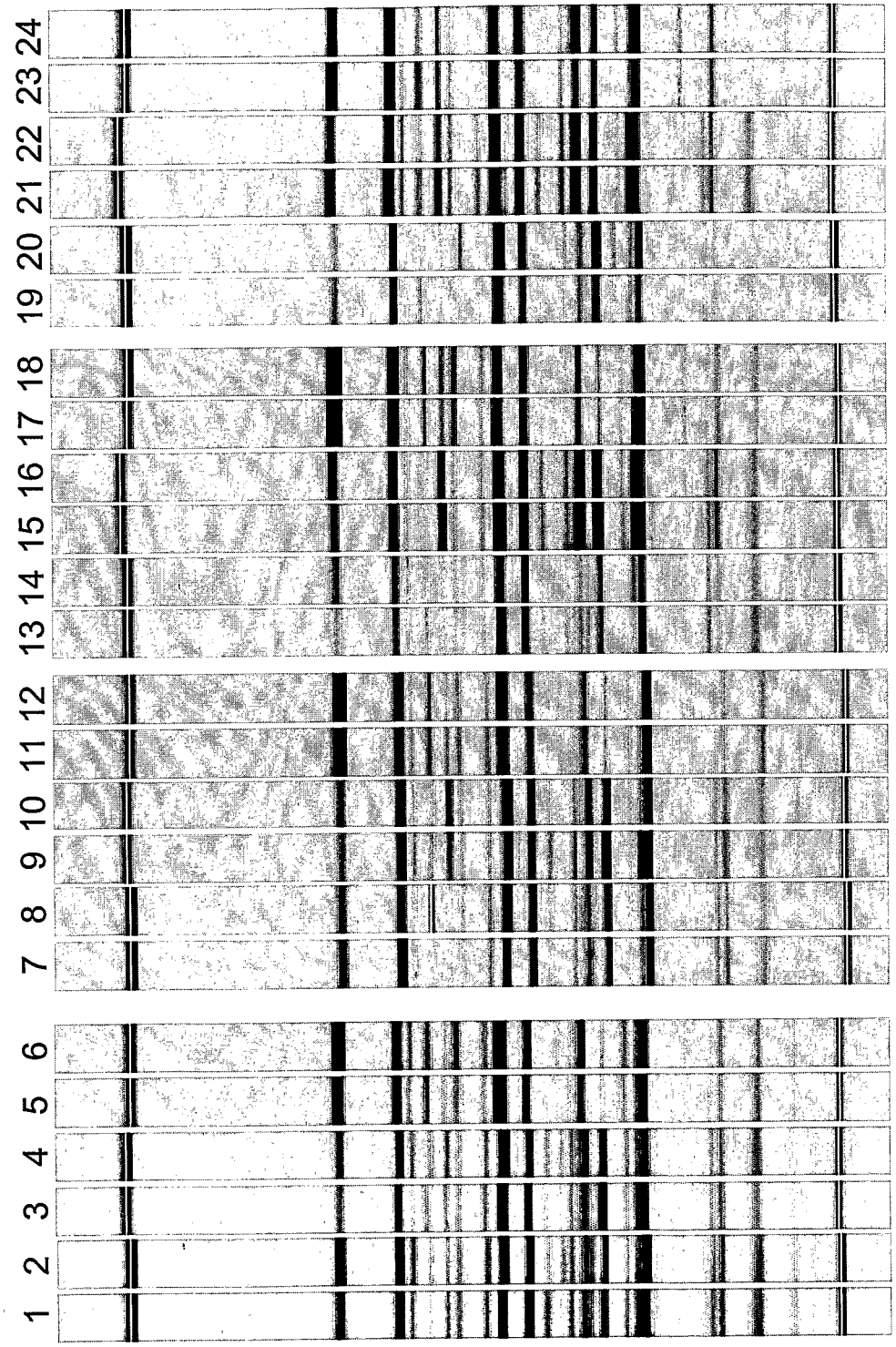
Figure 5:
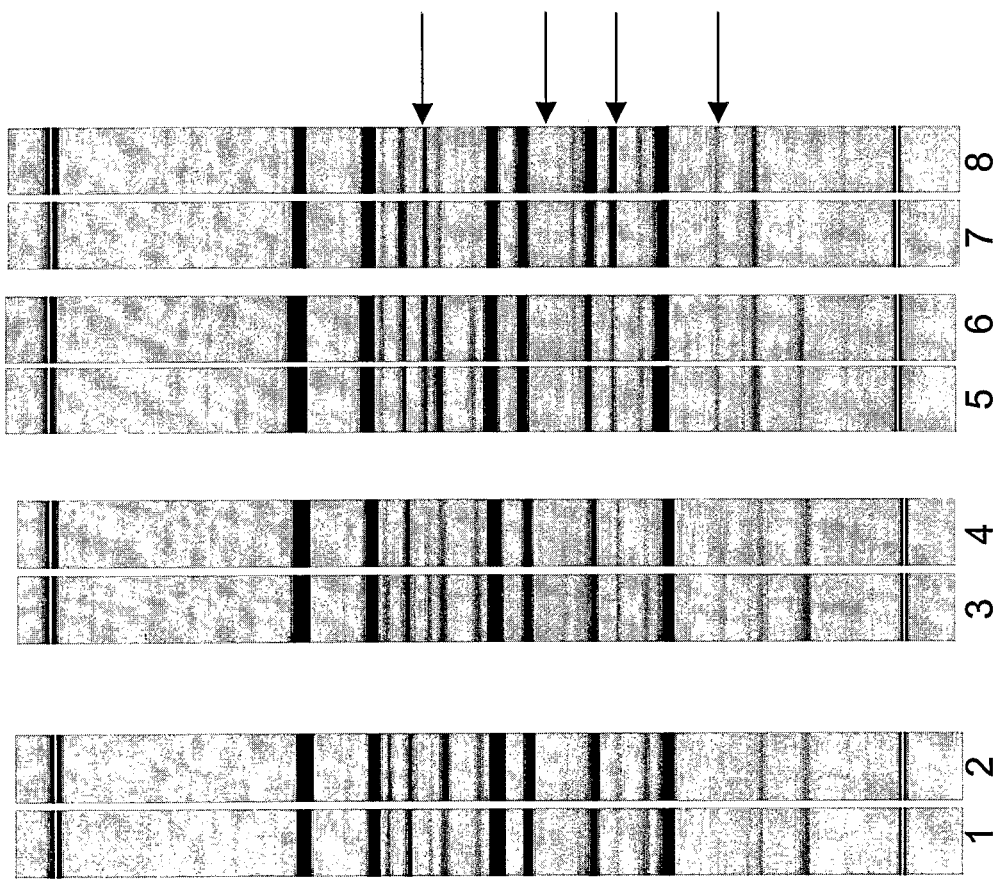
Figure 6:
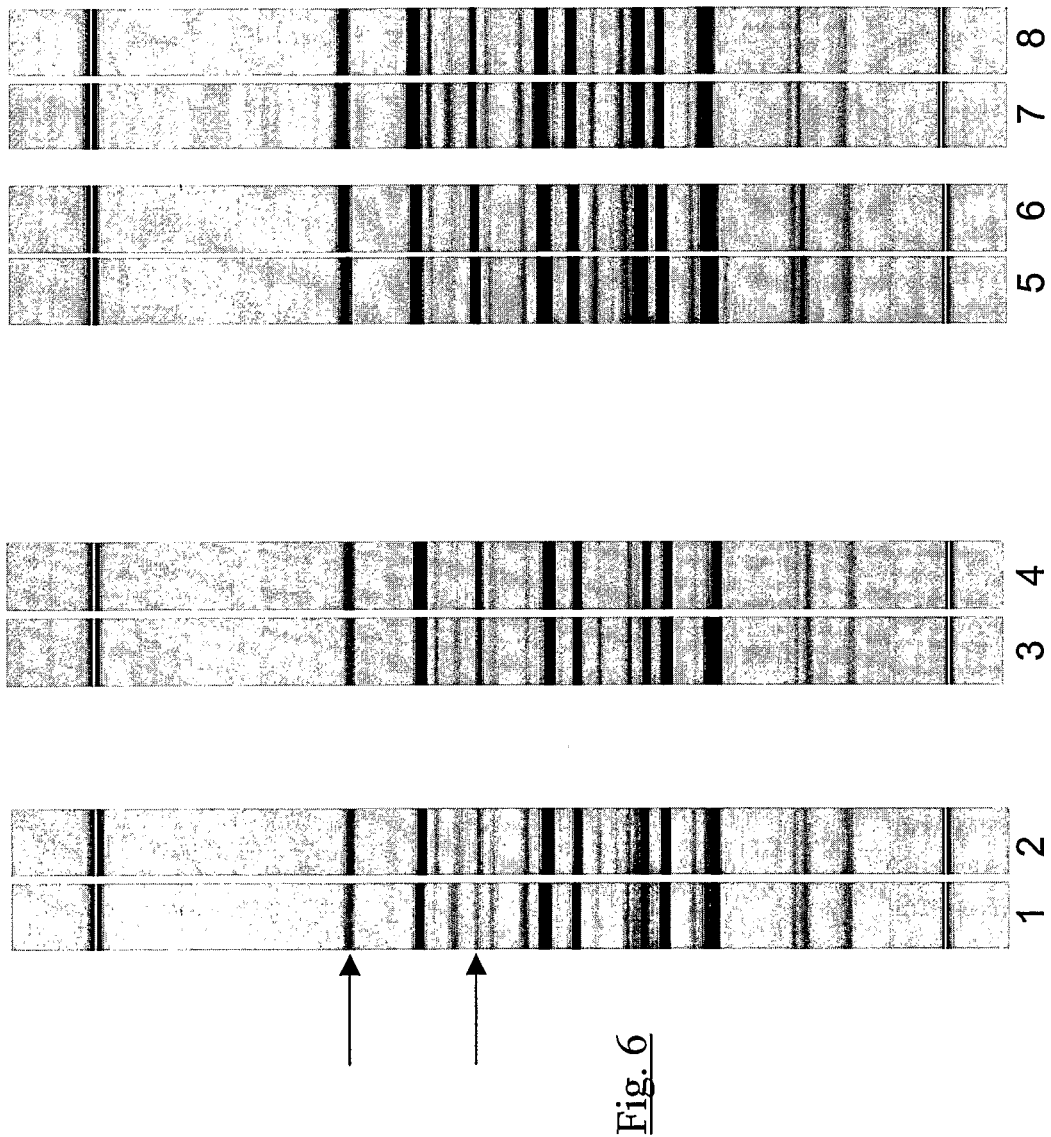

In an alternative aspect of the invention, the cells of the wound healing composition have a banding pattern of PCT products resulting from differential display identical or similar to that shown in FIG. 4, FIG. 5 or FIG. 6 for samples less than 21 days old.

The present inventors have found that different methods as described herein can be used to identify a gene expression profile characteristic of a composition which has a wound healing phenotype. The genes are expressed at the given levels in various conditions while maintaining the wound healing phenotype.

The invention provides an approach to treatment of chronic wounds based on delivering cells with the potential to promote and accelerate the healing process. Although developing a viable, multilayered skin equivalent (for example, appropriate cell types organised into functional and anatomically relevant structures) remains a worthwhile goal, so far this has proven elusive. However, for many situations, the present invention shows that such an approach may be unnecessarily complex and that a simpler solution, that of simply providing cells at the appropriate stage of development and exhibiting a particular phenotype in a wound-healing composition for rapid, convenient and accurate application to wounds, is remarkably effective. The cells used in the present invention develop surprisingly rapidly to have a wound healing phenotype, which phenotype is characterised by the level of gene expression or the differential display banding as indicated herein, to encourage immediate wound healing. It is believed that the wound healing phenotype represents the optimal phenotype for accelerating or assisting wound healing. The invention allows delivery of such cells (in the composition) to a wound, preferably in a manner which is consistent with the maintenance of the wound-healing phenotype.

Whether or not cells in a composition have a wound healing phenotype may also be tested by applying the composition to a wound (as defined herein) and observing whether or not healing of the wound is accelerated or assisted.

In a preferred embodiment, semi-quantitative or quantitative PCR (TaqMan®) may be used to measure the amounts of particular genes being expressed by the cells of the composition. The present inventors have assayed various genes as indicated in the specific embodiments given below and have shown that there is a subset of genes which can be deemed to be characteristic of the wound healing phenotype.

The level of gene expression is measured according to the first aspect of the invention in terms of fold increase compared to the expression level of the "housekeeping gene" RPL32, i.e. the multiple by which expression of a gene is higher than that of RPL32. A housekeeping gene is one whose expression is largely independent of intrinsic and extrinsic factors that might influence gene expression and thus serves as a point of standardisation for genes whose expression may vary according to such factors. Thus, comparison of gene expression to a housekeeping gene provides an indication of gene expression level which is independent of factor such as starting conditions, amounts of RNA, or amounts of product. The expression levels of both RPL32 and the genes of interest can be measured using standard methodology, available to the skilled person, such as PCR, quantitative PCR and/or Northern blot. A microarray may also be used to determine expression levels of specific genes and/or global gene expression patterns. It is possible using microarrays to assess the expression of a large sample size of up to 20,000 genes expressed by cells such as human cells.

Other genes which may be screened or used to characterise a wound healing phenotype include those encoding cytokines, metabolic genes, cytoskeletal genes, cell surface molecules and cell signalling molecules.

Through analysis of gene expression, it has been observed that the four genes defined above are indicative of a cellular phenotype which is effective at accelerating or assisting wound healing, i.e. a wound healing phenotype. The expression of these genes has been observed to be independent of storage temperature (for a limited time period), and thus the wound healing profile of the cells is maintained throughout storage and shipping which may take place during that time period.

Differential display is a PCR-based method using non-specific primers, which produces a banding pattern when run on a gel that is unique to the sample of interest. This results in a "barcode" type pattern of gene expression. An advantage of this process is that it produces an easily recognisable pattern that can be analysed without numerical manipulation, or knowledge of the actual genes involved. The differential display pattern as shown in FIG. 4 and/or FIG. 5 for fibroblasts cells incubated in fibrin has been found to be characteristic of a wound healing phenotype. Display patterns similar, i.e. with at least 75 to 99%, preferably at least 90 to 99%, of the same expression bands, are within the scope of the present invention.

From the experiment resulting in the differential display banding pattern shown in FIGS. 4 to 6, relevant bands deemed to be indicative of a wound healing phenotype were isolated and sequenced. The PCR products isolated had the following molecular weights and were labelled as follows:

| | |
|---|---|
| 227 bp | DD2 |
| 347 bp | DD4 |
| 333 bp | DD5 |
| 128 bp | DD10 |
| 478 bp | DD12 |
| 157 bp | DD13 |
| 396 bp | GB1 |
| 398 bp | GB5. |

Wound healing cells expressing nucleic acids encoding the above genes may fall within the scope of the invention even if the PCR products differ in size from those indicated in the figures. The cells having the desired phenotype will typically express one or more of these genes under particular conditions or at a particular age, as shown in Table 4 and Table 5 below.

The cells of the composition may further exhibit a 1 to 500-fold, more preferably a 13 to 160-fold, higher level of expression of "X-ray repair, complementing defective, in Chinese hamster, 1" (DD5) than of RPL32; and/or exhibit a 1 to 210-fold, more preferably a 3 to 15-fold, higher level of expression of a gene deposited as Genbank Accession No. gi|10437022 (DD10) than of RPL32; and/or exhibit a 1 to 33-fold, preferably a 1 to 5-fold, higher level of expression of a gene deposited as Genbank Accession No. gi|12410897 (GB1) than of RPL32.

Where the composition after development of the wound healing phenotype is maintained at a temperature of between about 20° C. to 42° C., preferably about 37° C., the cells may further exhibit a 1000 to 120000-fold, preferably a 11000 to 53000-fold, higher level of expression of ribosomal protein S24 (GB5), and/or exhibit a 120 to 36000-fold, preferably a 1000 to 30000-fold, higher level of expression of ribosomal protein S8 (DD12) than of RPL32, and/or exhibit a 0 to 750000-fold, more preferably a 1 to 136000-fold, higher level of expression of a gene deposited as Genbank Accession No. gi|7022020 (DD2) than of RPL32.

Where the composition after development of the wound healing phenotype is stored at a temperature of 2° C. to 8° C., for example 3° C. to 5° C., preferably about 4° C., the cells may further exhibit a 130 to 760-fold higher level of expression of urokinase (PLAU), and/or exhibit a 28000 to 2065000-fold higher level of expression of vimentin (Vim) than of RPL32.

The living cells may be incubated within a protein-rich environment for up to about 14 days to allow development of the wound healing phenotype.

The protein-rich environment may comprise any of the group consisting of fibrin, collagen, fibronectin, vitronectin, alginate, agar, hyaluronic acid, modified starches, carrageenans, carob, gelatine, pectin and gelling agents.

The protein-rich environment is preferably a support matrix. The cells may be suspended within the matrix, preferably substantially uniformly within the matrix.

The matrix of the composition may be "pre-cast" in the sense that it is provided as a solid or semi-solid form (such as a gel). The matrix may be insoluble. Most preferably, the cells are cast in the matrix prior to development of a wound healing phenotype.

The rate of fibrinolysis occurring within the composition may be a factor taken into account with a fibrin matrix-based composition. As described above, fibrinolysis is a normal part of the wound healing process, by which the fibrin matrix is gradually replaced by other extracellular matrix proteins. If, however, fibrinolysis occurs too early or too rapidly, the wound healing gel is broken down before useful collagen deposition has occurred. Fibroblast expression of pro-fibrinolytic factors such as urokinase-type plasminogen activator is developmentally regulated and so the phenotype of fibroblasts where included in the composition is relevant if premature fibrinolysis is to be avoided.

The wound healing composition may further comprise a protease inhibitor suitable for preventing breakdown of the matrix. The inhibitor may be a serine protease inhibitor, most preferably one or more selected from the list consisting of aprotinin, e-aminocaproic acid and tranexamic acid. Preferably, especially where the concentration of protein is in the range 7 to 12 mg.ml$^{-1}$, the protease inhibitor is aprotinin.

Alternatively, especially where the concentration of protein is in the range 3 to 5 mg.ml$^{-1}$, the protease inhibitor may be tranexamic acid.

The matrix may be protein-based, for example having a protein concentration in the range of about 3 to 12 mg.ml$^{-1}$.

The matrix of the wound healing composition is preferably a fibrin matrix. The fibrin may be present in a concentration in the range of 3 to 12 mg.ml$^{-1}$, for example 7 to 12 mg.ml$^{-1}$ or 3 to 5 mg.ml$^{-1}$. The fibrin matrix is preferably formed by thrombin-mediated polymerisation of fibrinogen.

The matrix is preferably non-pyrogenic and/or sterile.

The cells may be cast into the support matrix before incubation.

The matrix is preferably solid or semi-solid.

The composition may be stored for up to about 40 days, preferably up to 19 days and more preferably about 7 to 14 days or about 7 to 11 days at a temperature of 2° C. to 8° C., for example 3° C. to 5° C., preferably about 4° C., while retaining the wound healing phenotype. The composition in this embodiment therefore does not require freezing, as do certain prior art wound healing compositions. The present composition preferably does not contain a substance added as a cryopreservant or cryoprotectant (such as glycerol and/or human serum albumin).

Once the cells of the composition have been incubated to reach or approach a wound healing phenotype phase, the composition can preferably conveniently be stored at approximately 4° C. for up to 40 days, and certainly 7 to 14 days, before use without significant loss of viability or change of phenotype. This has significant practical advantages in that it provides not only an efficacious product comprising cells with a wound healing phenotype (for example cells that are optimally suited for secretion of extracellular matrix with minimal inappropriate fibrinolysis), but also gives a relatively long shelf-life under commonly available standard refrigeration conditions. The ability to ship such products at approximately 4° C. also considerably simplifies transportation. Maintaining a cold chain at 2° to 8° C. is considerably simpler and cheaper than shipping at −70° C., as is commonly required for live cells.

The cells are preferably mammalian, for example human.

Cells of the present invention unless indicated otherwise may include fibroblasts, keratinocytes, stratum germinativum cells, and combinations or admixtures of such cells. However, in a preferred embodiment, the cells of the composition may substantially exclude keratinocytes. The cells may be isolated from any suitable mammalian source, and preferably are human. The cells are preferably allogeneic, although autologous and/or xenogeneic cells may be used. The cells may be substantially of one type only, for example 90% to 100%, preferably 95% to 99.5%, and more preferably 97.5% to 99% of one type. In a preferred embodiment, the cells are substantially fibroblasts, for example 90% to 100%, preferably 95% to 99.5%, and more preferably 97.5% to 99% fibroblasts. The fibroblasts may be dermal fibroblasts, preferably human dermal fibroblasts. A preferred embodiment comprises allogeneic human foreskin-derived fibroblasts.

As required for manufacture, cells may be thawed, recovered, expanded in culture (for example, for about a week) or until they reach confluence, and resuspended in appropriate volumes and densities as required. Although early passage cells are preferred, later passage cells may also be used. Preferably the cells have undergone less than 20 passages, more preferably less than 15 passages, most preferably less than 10 passages, for example 7 passages. Once defrosted for use in the present invention, the cells may be incubated further as described.

For the purposes of the present invention, day 0 is the day on which the cells are incubated and begin development and they will reach a wound healing phenotype within the timeframe described above (for example, up to 4 days, or 96 hours, after day 0).

The cells of the composition in one embodiment substantially exclude keratinocytes.

In a preferred embodiment, the cells are human dermal fibroblasts within a sterile, non-pyrogenic support matrix formed by thrombin-mediated polymerisation of fibrinogen, and in which the composition has been incubated for 16 to 24 h at about 37° C.

The present inventors have also analysed gene expression levels following normalisation according to the amount of starting material (typically mRNA or cDNA) used to quantify gene expression and normalisation to a level of gene expression by fibroblasts in liquid medium. By comparing gene expression levels of various genes over time between a preferred embodiment of the invention, a wound healing composition comprising fibroblasts in a fibrin matrix, with another embodiment comprising fibroblasts in a collagen matrix and a further embodiment comprising fibroblasts in a liquid culture medium, the inventors were able to identify that specific genes had significantly higher expression levels in the fibrin matrix than the other embodiments.

Therefore, in a further aspect of the invention there is provided a wound healing composition comprising fibroblasts cultured within a fibrin matrix, in which the fibroblasts of the composition have a wound healing phenotype and have a higher level of expression of collagen 6a1 (Coll6a), apolipoprotein D (APOD), collagen 3a1 (Coll3a1), ribosomal protein L32 (RPL32), plasminogen activator inhibitor (PAI), urinary plasminogen activator (PLAU), vimentin (Vim), smooth muscle actin (SMA) and cyclo-oxygenase 2 (Cox2) than fibroblasts cultured in a collagen matrix and fibroblasts cultured in medium without a matrix.

The fibroblasts of the composition may have approximately a 3-fold higher level of expression of Coll6a, and/or a 8-fold higher level of expression of APOD, and/or a 80-fold higher level of expression of Coll3a1, and/or a 3-fold higher level of expression of RPL32, and/or a 3-fold higher level of expression than PAI, and/or a 20-fold higher level of expression of PLAU, and/or a 20-fold higher level of expression of Vim, and/or a 5-fold higher level of expression of SMA, and/or a 8000-fold higher level of expression of Cox2, than fibroblasts cultured in a collagen matrix.

The fibroblasts of the composition may additionally or alternatively have approximately a 4-fold higher level of expression of Coll6a, and/or a 4-fold higher level of expression of APOD, and/or a 10-fold higher level of expression of Coll3a1, and/or a 2-fold higher level of expression of RPL32, and/or a 3-fold higher level of expression than PAI, and/or a 30-fold higher level of expression of PLAU, and/or a 10-fold higher level of expression of Vim, and/or a 2-fold higher level of expression of SMA, and/or a 5000-fold higher level of expression of Cox2, than fibroblasts cultured in medium without a matrix The fibroblasts of the composition may have a higher level of expression of matrix metalloprotease 2 (MMP2), insulin induced gene 1 (INSIG1), growth arrest specific gene 6 (Gas6) and collagen 1a1 (Coll1a) than fibroblasts cultured in a collagen matrix. For example, the fibroblasts of the composition may have approximately a 2-fold higher level of expression of MMP2 and/or INSIG1 and/or Gas6 and/or Coll1a than fibroblasts cultured in a collagen matrix.

The fibroblasts of the composition may have a higher level of expression of glyeraldehyde-3-phosphate dehydrogenase (GAPDH) than fibroblasts cultured in medium without a matrix. For example, the fibroblasts of the composition may have approximately a 3-fold higher level of expression of GAPDH than fibroblasts cultured in medium without a matrix.

The composition may be incubated for up to about 14 days, or up to about 8 days, preferably about 96 h, for example up to 72 h, 48 h, 25 h or 24 h, and more preferably for 16 h to 24 h, to allow development of the wound healing phenotype. The composition is preferably incubated at a temperature of about 37° C. to allow development of the wound healing phenotype. If incubation takes place at a lower temperature, the living cells will develop at a slower rate and incubation time may need to be extended. Incubation is preferably in vitro, but may also be in situ (for example, with the composition applied to a wound).

In one embodiment, it has been found by the present inventors that taking cells such as passaged human dermal fibroblasts, casting (or seeding) the cells in a matrix such as a protein-based matrix and then incubating this mixture for up to 96 h, for example, results in a wound healing phenotype as defined herein that is particularly beneficial for use in wound healing applications. It has been observed that such cells are predominantly in a proliferative phase in culture (encouraged by low density seeding, avoiding contact inhibition).

The present inventors have found that under normal culture conditions, for example, a liquid culture of human dermal fibroblasts incubated in a standard culture medium at 37° C., development of a wound-healing phenotype may typically take 2 to 3 days. However, incubation of such fibroblasts in a suitable environment such as in a support matrix and/or a wound shortens the development process, so that before 24 hours the cells may have entered or reached the wound-healing phenotype. Thus, incubation of cells in a suitable support matrix and/or wound may result in a shorter development time to reach a wound healing phenotype than standard (for example, liquid) culture conditions.

Preferably, the composition excludes mitotically inactivated cells (for example cells mitotically inactivated by administration of mitomycin C or other chemically-based mitotic inhibitors, irradiation with γ-rays, irradiation with X-rays, or irradiation with UV light, as described for example in US2003/0165482).

The cells of the wound healing composition may be actively synthetic or able to become actively synthetic rapidly (for example, following storage). The cells are in a preferred embodiment not proliferating and/or not senescent. Optimally the cells must be in a synthetic phase of development (or maturity), rather than a proliferative or senescent phase. Proliferation may be useful to increase cell numbers, but delays the important synthesis of extracellular matrix proteins such as collagen types I and III, fibronectin and vitronectin. Cells that have become senescent do not contribute to wound healing and so serve little purpose as such a therapeutic.

Where the composition is sufficiently solid, it may be provided in any suitable shape and size, to suit the wounds it is design to be used with. Preferably, the composition is substantially disk-shaped. The composition may have a thickness of approximately 8 mm or less, preferably 5 mm or less. The thickness of the matrix will normally determine the thickness of the composition.

The wound healing composition may comprise about 450 to 2500 cells per $mm^2$, for example about 750 to 2000 cells per $mm^2$, preferably about 900 to 1700 cells per $mm^2$ such as about 1500 cells per $mm^2$, or for example about 450 to 550 cells per $mm^2$ and preferably about 500 cells per $mm^2$. Lower cell densities than those indicated may result in poor cell viability. Higher cell densities may result in inhibition of extracellular matrix protein synthesis and progression to a senescent cell phenotype. Within the range of cell densities provided above, specific embodiments of the invention have been developed using approximately 500 cells per mm$^2$ and approximately 1500 cells per mm$^2$.

The wound healing composition is preferably single-layered. The term "single-layered" indicates that the composition preferably has only one layer containing cells within a support matrix, i.e. it is not a multi-layered "skin equivalent" with multiple layers of (different) cells. The invention also encompasses compositions having additional non-cellular layers as well as compositions having stacked layers comprising substantially uniform single layers.

The composition may be packaged in a container suitable for transporting the composition (for example, while storing the composition) and/or topically applying the composition to a skin surface. The container may comprise a flexible pouch consisting of two sheets of impermeable flexible material peripherally sealed to provide a means of containment for the composition, the pouch comprising a first internal surface to which the composition is adherent at a level of adhesion more than that between the composition and a second internal surface of the pouch but less than that between the composition and the skin surface, such that in use the pouch may be opened by parting the sheets and the composition conveniently manipulated and directly applied to the skin surface without further requirement for the composition to be touched directly by any other means prior to application. For example, the container may be an Oliver® Products Company "Solvent Resistant Peelable Pouching Material" (Product number Q15/48BF1).

In a further aspect of the invention there is provided a wound healing composition as described herein for use as a medicament. For example, the composition may be for use as a medicament in the treatment of a skin lesion. The composition as a medicament may be used for topical application to a skin lesion or wound such as a venous ulcer, diabetic ulcer, pressure sore, burn or iatrogenic grating wound. The composition is particularly useful for treating recalcitrant wounds, i.e. wounds which have not healed within three months using standard treatment.

In another aspect of the invention there is provided a method of manufacturing a wound healing composition as defined herein, comprising the steps of:
suspending living cells in a protein-rich environment; and incubating the cells under conditions (for example, conditions as defined herein, such as temperature and time conditions) which allow development of a wound healing phenotype in the cells, thereby forming the wound healing composition.

The cells may be suspended in a solution comprising a polymerisation agent and/or a monomer capable of being polymerised by the polymerisation agent into a matrix, and in which the method comprises a further step of forming a single-layered support matrix comprising the cells by polymerisation of the monomer with the polymerisation agent prior to incubating the cells. Here, the matrix may be formed by adding monomer or polymerisation agent to the solution such that both monomer and polymerisation agent are present in sufficient concentrations to effect polymerisation.

In another aspect of the invention, there is provided a method of manufacturing a wound healing composition as defined herein, comprising the steps of forming a single-layered support matrix by polymerising a polymerisable monomer with a polymerisation agent, casting living cells into the support matrix, and incubating the matrix under conditions (for example, conditions as defined herein, such as temperature and time conditions) which allow development of a wound healing phenotype in the cells, thereby forming the wound healing phenotype.

Preferably, the monomer is fibrinogen and the polymerisation agent is thrombin. Alternatively, the polymerisation agent may be vitamin K-dependent clotting factors, venom serine proteases (for example, Crotalax, Batroxobin, Gabonase, Okinaxobin, Reptilase, Calobin and Fibrozyne) or other agents with thrombin-like fibrinogen cleaving activity.

The cells may have a wound healing phenotype as described herein prior to being suspended in the monomer, or may adopt or develop into such a phenotype during incubation within the time-frames described herein (for example, within 0 h to 96 h after suspension).

The methods may include steps adding additional components as described herein to the composition.

Polymerisation may occur in a mould.

The method of manufacture may comprise a further step of packaging the wound healing composition into a container for storing the composition and/or for transporting the composition and/or for topically applying the composition to a skin surface of a patient.

Also provided according to the invention is the use of living cells as defined herein in the manufacture of a wound healing composition as defined herein for the treatment of a skin lesion.

In a further aspect of the invention, there is provided a method of treating a patient suffering from a skin lesion comprising topically applying of a wound healing composition as defined herein to the skin lesion.

The invention also provides a method of determining whether a composition comprising living cells has a wound healing phenotype, comprising the steps of:
(i) quantifying the cellular expression of genes as defined herein; and
(ii) comparing expression level of the genes compared to expression level of RPL32, thereby determining whether the composition has a wound healing phenotype.

In an alternative aspect of the invention there is provided a method of determining whether a composition comprising living fibroblast cells within a fibrin matrix has a wound healing phenotype, comprising the steps of:
(i) quantifying the expression of genes as defined herein in the cells of the composition and in fibroblasts cultured in a collagen matrix and in fibroblasts cultured in medium without a matrix; and
(ii) comparing expression level of the genes, thereby determining whether determining whether the composition has a wound healing phenotype.

The invention also provides a method for conducting a business, comprising the step of determining whether a composition has a wound healing phenotype according to either of the above methods.

In a further aspect, the invention provides a container (or package) for a solid or semi-solid, sterile, topical composition (preferably a wound healing composition as described herein) comprising a flexible pouch consisting of two sheets of impermeable flexible material peripherally sealed to provide a means of containment for the composition, the pouch comprising a first internal surface to which the composition is adherent at a level of adhesion more than that between the composition and a second internal surface of the pouch but less than that between the composition and a bodily surface to be treated, such that in use the pouch may opened by parting said sheets and the composition conveniently manipulated and directly applied to the bodily surface without any requirement for the medicament to be directly touched by any other means before application. The container per se aspect of the invention may exclude the Oliver® Products Company "Solvent Resistant Peelable Pouching Material" (Product number Q15/48BF1).

In a further aspect, there is provided use of a container as described herein for storing, transporting and/or applying a solid or semi-solid, sterile, topical composition (preferably a wound healing composition as described herein).

The container provides a convenient means of storage, delivery and application of any form of solid or, especially, semi-solid, materials, especially those intended for topical application to bodily surfaces. Preferably such materials are of a semi-solid or gel nature, such that physical manipulation would without the container be difficult. The preferential adherence of the material to an element of the container, with the ease of transfer thereafter to the skin or other bodily surface, provides a considerable advantage. In particular, such materials may be cut to the required size before application to the intended area. In the case of wound healing compositions as herein described, this is a particular advantage.

In a preferred embodiment, the container comprises metal foil, laminated or metalised plastic. In one preferred embodiment it comprises a transparent area allowing visual inspection of its contents.

Preferably, the internal surfaces of the container and its contents are sterile.

In a preferred embodiment, the first internal surface of the pouch is modified to increase the adherence of the composition thereto. In one embodiment this comprises application of a coating to the first internal surface. Preferably the coating is selected from the list consisting of: a polymer, a thermoplastic, a thermo-setting plastic, a protein, an amino acid, a carbohydrate.

Alternatively, the first internal surface is modified by roughening to increase the adherence of the composition thereto. As used herein, the term "roughening" includes any physical modification of the surface intended to improve adherence, such as embossing, scratching, abrading or scuffing, or chemical roughening by means of etching, erosion, acid or alkali treatment. Other means of modifying the surface energy properties of the surface in order to improve or modulate the degree of adherence of the solid or semi-solid product are disclosed. Such means include coating the first internal surface of the pouch. Preferably such a coating is selected from the list consisting of a polymer, thermoplastic, thermo-setting plastic, protein, amino acid or carbohydrate.

In one particularly preferred embodiment, the first internal surface is modified by means of a discontinuous coating, in the form of raised areas or dots, having the effect of providing a roughened surface.

Also provided according to the present invention is a method of packaging a sterile, solid or semi-solid topical composition as described herein comprising the step of placing the composition in a container pouch as described herein.

Figure 3:
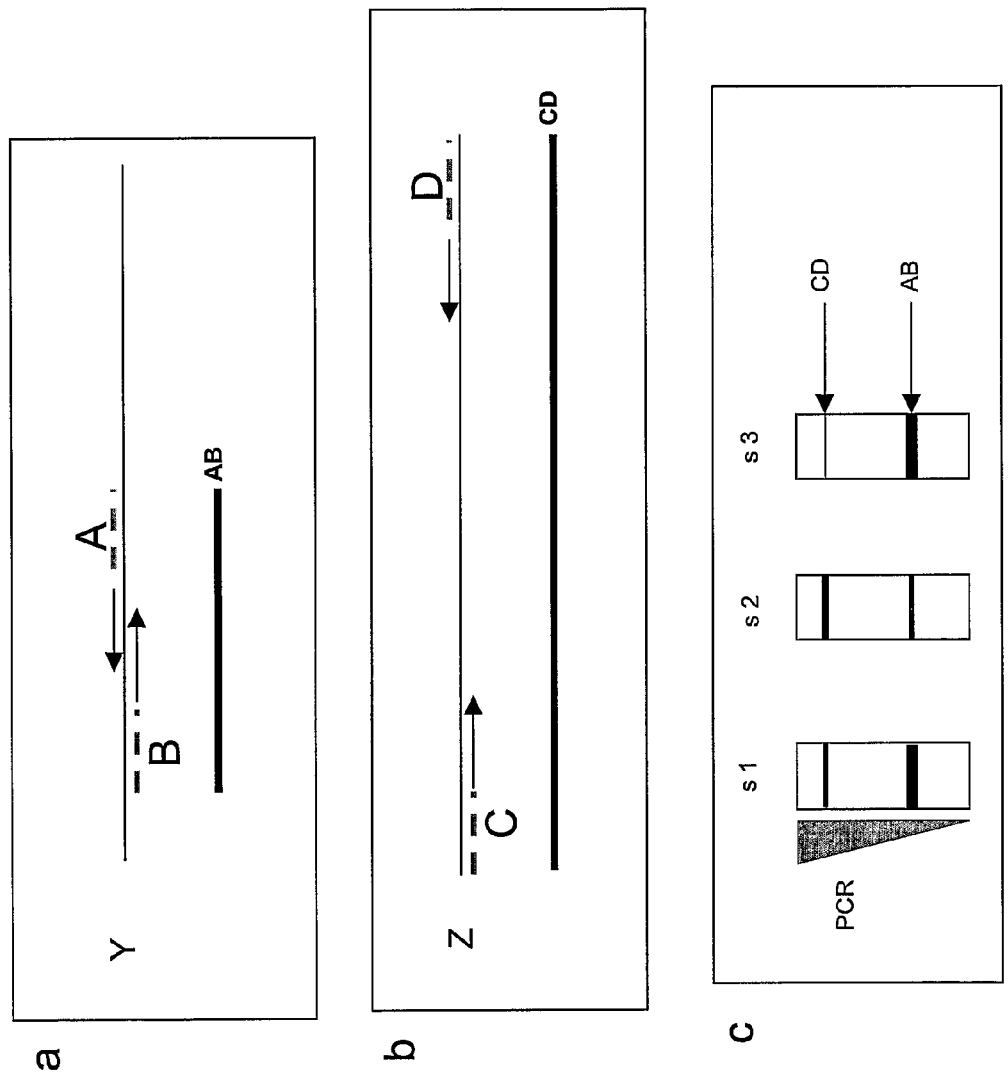
Figure 7:
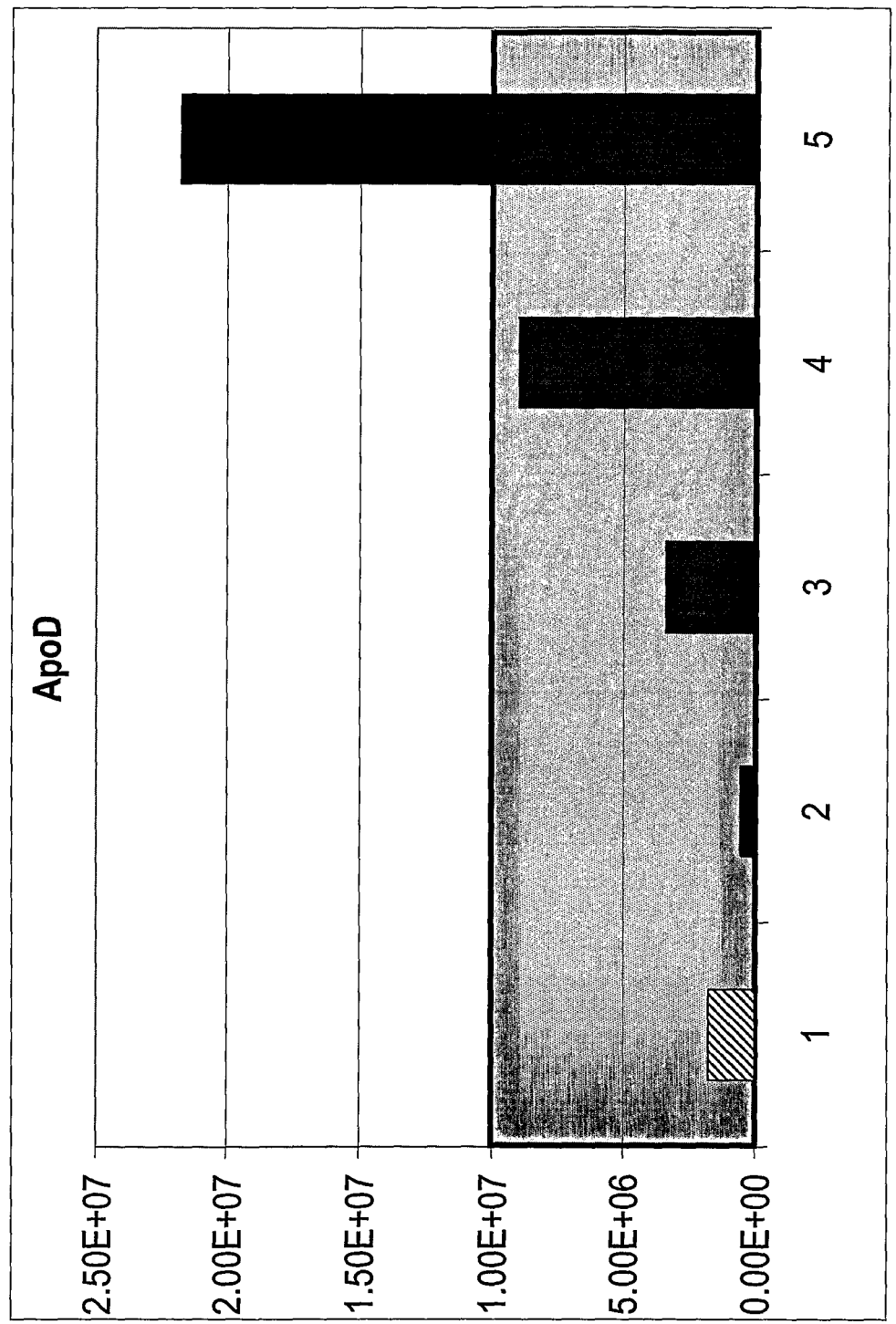
Figure 8:
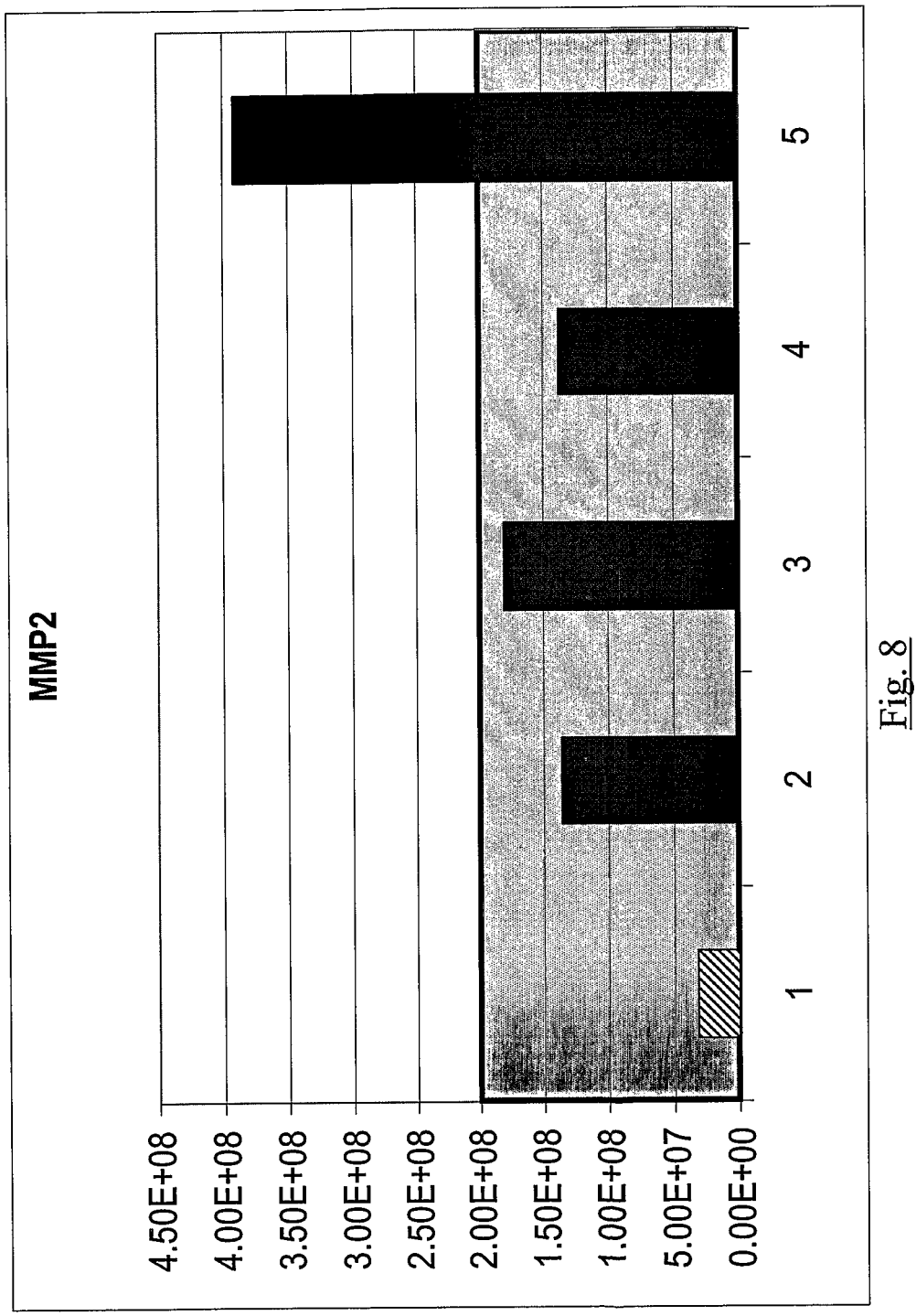

Specific examples of the invention will now be described with reference to the accompanying figures, in which:

FIG. 1 is a flow chart summarising a process of manufacturing a wound healing composition according to preferred embodiments of the invention;

FIG. 2 shows the packaging, manipulation and application of a preferred wound healing composition produced according to a process shown in FIG. 1. A: shows a matrix (or set gel) preferentially adhering to a modified internal surface of one of two metalised plastic sheets of a container pouch. B: shows the use of one of the sheets of the container to apply the gel of the wound healing composition to skin. Note that the sheet may used to support the gel while both are cut to the appropriate shape and size. C: shows the wound healing composition in place;

FIG. 3 is a diagrammatic representation of the differential display process (prior art);

FIG. 4 shows an example of a "bar code" as revealed by differential display of polyA cDNA products between samples cast into rat-tail collagen (lanes 1, 2, 7, 8, 13, 14, 19, 20), onto tissue culture plastic in no exogenous matrix (lanes 3, 4, 9, 10, 15, 16, 21, 22) or into fibrin (lanes 5, 6, 11, 12, 17, 18, 23, 24) and RNA sampled from each matrix/condition on 1 (lanes 1-6), 5 (lanes 7-12), 14 (lanes 13-18), or 21 (lanes 19-24) days after casting;

FIG. 5 shows a "bar code" of comparative of gene expression, as revealed by differential display, of cells in fibrin 1 (lanes 1 and 2), 5 (lanes 3 and 4), 14 (lanes 5 and 6), and 21 (lanes 7 and 8) days after casting. Arrows indicate specific PCR products that increase with increasing time from casting;

FIG. 6 shows a "bar code" comparison of gene expression, as revealed by differential display, of human dermal fibroblast cells cast onto tissue culture plastic 1 (lanes 1 and 2), 5 (lanes 3 and 4), 14 (lanes 5 and 6), and 21 (lanes 7 and 8) days after casting. Arrows indicate specific PCR products that increase with increasing time from casting;

FIG. 7 shows a graph comparing expression of Apolipoprotein D (ApoD) in HDFs cast in fibrin, collagen and onto tissue-culture appropriate plastic and stored at 4° C. (sample 1) or at 37° C. for 1 (sample 2), 5 (sample 3), 14 (sample 4), or 21 (sample 5) days. The shaded area on the graph represents the range of expression specific to the profile of young cells and the profile for storage/shipping conditions of the product of the invention;

FIG. 8 as FIG. 7 for Matrix Metalloproteinase 2 (MMP2) gene; and

Figure 9:
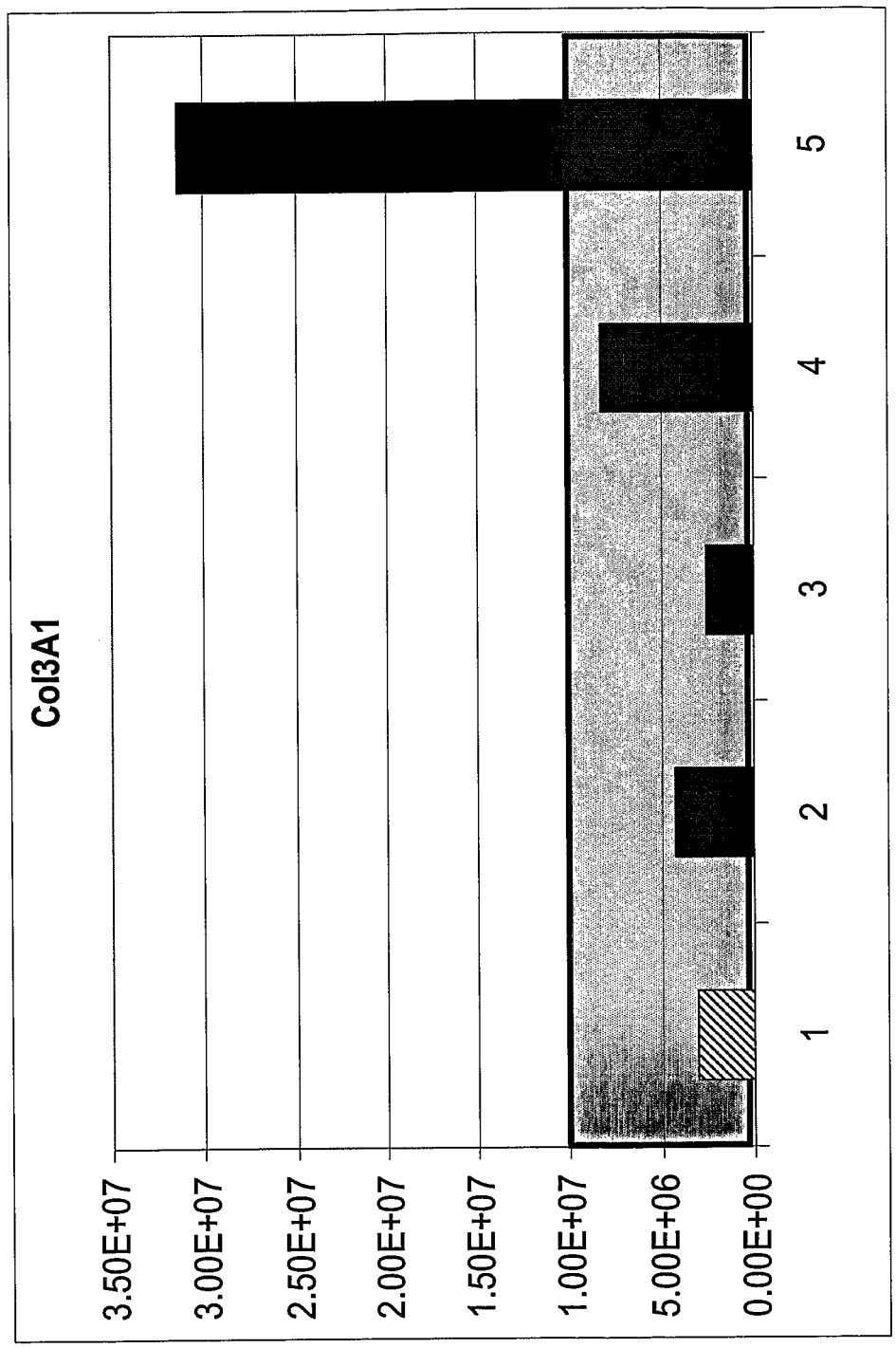

FIG. 9 as FIG. 7 for collagen 3A1 (coll3a11) gene.

The process of manufacturing preferred compositions of the invention is summarised in FIG. 1. Alternative components or methods as described above may be used in place of those described here.

In principle, the composition comprises two components, which are cast together. The first component comprises a solution of fibrinogen together with one or more protease inhibitors to prevent unwanted proteolysis by protease contaminants and premature matrix breakdown by cells during storage. In particular, contaminants may include the naturally fibrinolytic enzyme plasmin, or its precursor plasminogen. Serine protease inhibitors such as aprotinin, e-aminocaproic acid, or its analogue tranexamic acid, are frequently used in order to inhibit plasmin or prevent its activation. Added to this fibrinogen solution is a suspension of living cells in a suitable medium or buffer solution (a "working cell suspension").

The second component comprises a solution of thrombin (an enzyme that naturally acts upon fibrinogen), calcium ions (a required cofactor), and a medium suitable for the culture of living cells. A further clotting factor, Factor XIII, is also activated by thrombin in the presence of calcium ions. Activated Factor XIII promotes polymerisation of monomeric fibrin (cleaved from fibrinogen by thrombin) into a three-dimensional protein insoluble scaffold.

In order to cast a gel (i.e. a matrix in the form of a gel), these two components are combined and, whilst still liquid, poured into a pre-coated suitable mould. Although commonly circular, the gels may be cast into any desired shape. For some applications, other shapes may be more suitable. In particular, essentially or substantially rectangular or elliptical gels may be more convenient for larger wounds.

Enzymatic cleavage of fibrinogen into fibrin monomers and polymerisation of these monomers results in setting of the liquid into a semi-solid gel in which living cells are suspended. For many applications, this gel is then maintained for a period of about 24 hours under suitable conditions for cell growth, division and secretion of extracellular matrix proteins, and other proteins such as growth factors. Following development (or maturation), the cast gel is removed from the casting mould and placed directly into a sterile package (which term is taken herein to have the same meaning as "container"). A small amount of medium, for example a buffer medium, is added to each package to maintain the product during storage and shipping, and the packages are sealed. During storage and shipping the packages are maintained at a temperature of 2° C. to 8° C.

In two preferred embodiments, called Protoderm 500 and Protoderm 1500, the composition comprises cells at a density of about 500 cells per mm$^2$ and about 1500 cells per mm$^2$, respectively.

Advantages of such a product over the currently available alternatives include the following. The use of a protein sealant as a scaffold or support matrix allows convenient topical delivery of cells to the wound. The pre-cast gel allows convenient and accurate application of regenerative cells to the wound surface with control of the distribution and density of cells applied. Manufacture and shipping of other tissue equivalents may take approximately 3 weeks for the matrix alone, whereas the product of the present invention may be manufactured within 10 days, or even as little as 2 days if sufficient growing cells are available. These factors combine to give cost advantages, so manufacture and production is more cost effective than many other commercially available products.

As described below, the product of the invention when packaged also features a unique flat pack system (adhesive backing) ensuring maintenance of product during shipping and "ease of use" of final product. The precast gels can be shipped and stored for up to 28 days at 2 to 8° C., whereas other available products must either be frozen or shipped at room temperature.

EXAMPLE 1

High Protein Concentration Product ('Protoderm 500' and 'Protoderm 1500')

A first embodiment of the invention is designed to optimise both rapid manufacturing of the wound healing product and rapid wound healing by containing cells and protein components at relatively high concentrations.

Matrix

In the first embodiment, the matrix protein is fibrin, derived from a commercial fibrinogen product, Tisseel® (Baxter). When reconstituted, this provides a convenient two component system to which cells may be added. Components of the matrix are summarised in Table 1. It should be noted that Tisseel® also contains Factor XIII, as well as plasmafibronectin and plasminogen.

TABLE 1

Primary components of Tisseel [RTM]

| Component | Final concentration in cellularised scaffolds | |
|---|---|---|
| Matrix protein (fibrinogen) | 7.5-11.5 | mg/ml |
| Aprotinin | 300 | K IU/ml |
| Thrombin | 25 | IU/ml |
| Calcium chloride | 4 | mM |

As will be apparent to one of appropriate skill in the art, the concentrations of these components can be varied as required. For example, fibrinogen may be used in concentrations of the approximate range 7-20 mg.ml$^{-1}$ for this application, thrombin in the range 5-50 IU/ml (in fact, trace levels of contaminating thrombin may lead eventually to fibrin formation and gel setting without additional thrombin, but this is inconvenient and unpredictable), and calcium chloride in the range 2-20 mM. Aprotinin is used to prevent unwanted fibrinolysis but, again, the exact concentration may be varied.

Cells

Human dermal fibroblasts were obtained by culture of cells derived from neonatal foreskin tissue. Under GMP (Good Manufacturing Practice) conditions, fibroblastic cells were isolated by collagenase digestion and expanded by culture and serial passage according to routine laboratory practice to establish a master cell bank (MCB). The MCB was screened against a panel of human and animal-derived viruses, bacteria, mycoplasma and fungi, and for tumorigenicity by a GLP (Good Laboratory Practice)-accredited facility and determined to be free of contamination. Several working cell banks (WCB) were then established for manufacture of the product, rescreened and stocks of cells frozen according to standard procedures.

It is also envisaged that for various patient-specific applications, autologous fibroblasts or other cells obtained from biopsies may be cultured and expanded for use.

The cells were suspended in the quantities shown below (P-500 refers to Protoderm-500; P-1500 refers to Protoderm-1500) in Liebowitz L-15 cell culture medium buffered and supplemented as shown in Table 2 before addition to the fibrinogen component. As will be apparent to one of skill in the art, medium not intended for use in a $CO_2$-enriched atmosphere (commonly used in tissue culture incubators or sealed flasks) must be appropriately buffered by some other system. Such media, supplemented with, for instance, HEPES, are well-known in the art. Liebowitz L-15 medium relies on a phosphate buffering system. The medium was supplemented with sodium bicarbonate and dextrose, as shown.

For convenience and consistency, a standard 'working cell suspension' of $1.5 \times 10^6$ cells.ml$^{-1}$ was generally prepared.

Preparation of Fibrin Sealant

As outlined in FIG. 1 and summarised below, Tisseel® thrombin powder was reconstituted in a calcium chloride solution according to the manufacturer's directions.

Once dissolved, the Thrombin/CaCl$_2$ solution was further diluted with supplemented L-15 medium to obtain a 'Working Thrombin Solution' and refrigerated until further use for a minimum of 15 minutes. (Gels may also be manufactured with 'Working Thrombin Solution' at room temperature.) Freeze-dried fibrinogen was reconstituted with an aprotinin solution before being added to the working cell suspension in supplemented L-15 medium. Once reconstituted, the fibrinogen should be used within 4 h, ideally within 1 to 2 h.

Working thrombin solution (6.75 ml) contains:
Thrombin: 50 IU/ml (or 337.5 IU total)
Calcium chloride: 8 μmoles/ml (or 54 mmoles total)
In supplemented L-15
(Total Refers to the Amount in 6.75 mls)

Working fibrinogen and cell suspension mix (total volume 6.75 ml):
Tisseel: 19 mg/ml (or 128.25 mg total)
Aprotinin: 600 KIU/ml (or 4050 KIU total)
Cells: $1.2 \times 10^6$ cell/ml ($8.1 \times 10^6$ cells total for P-1500); or $0.4 \times 10^6$ cell/ml ($2.7 \times 10^6$ cells total for P-500)
in supplemented L-15
(Total refers to the amount in 6.75 mls)

TABLE 2

Details of Medium Used for Example 1

| Components (Supplier shown in parentheses) | Function | Concentration per ml |
|---|---|---|
| L-15 medium (Cambrex) | Nutrient delivery to the cellular component of the product. Maintains cell viability and structure of the gel. | N/A (base medium) |
| Sodium Bicarbonate (Mallinckrodt Chemical) | Required for cell viability | 202.5 μg |
| Dextrose (J.T. Baker) | Nutrient | 4.5 mg |
| Adenine (ABCR) | Base required for cell viability | 24.4 μg |
| L-Glutamine (Molekula) | Amino acid for cell viability | 0.29 mg |
| Ethanolamine (Molekula) | Phospholipid for cell metabolism | 6.2 μg |
| O-phosphoryl-ethanolamine (Merck) | Phospholipid for cell metabolism | 14.12 μg |
| Hydrocortisone (Spectrum Laboratory Products, Inc.) | Steroid required for cell metabolism | 0.4 mg |
| Human Recombinant Insulin (Serologicals) | Essential hormone | 5 μg |
| Selenious acid (Molekula) | Trace substrate for metabolism | 6.78 ng |
| 3,3',5-Triiodo-L-thyronine (ABCR) | Hormone | 1.35 ng |
| apo-Transferrin, bovine (Serologicals) | Cofactor for iron metabolism | 5 μg |
| Gamma Irradiated Foetal Bovine serum or New Born calf serum (JRH or Hyclone) | Nutrients | 2% v/v |

Note: As will be apparent to one of ordinary skill in the art, sources of ingredients used to producing the wound healing composition may differ depending on the grade or purity required for different applications. For example, for clinical applications of the product, pharmaceutical grade materials may be required.

Casting the Gels

The working thrombin solution (6.75 ml) and Tisseel® fibrinogen/cell suspension mixture (6.75 ml) were combined by means of a Duplojet mixer unit and loaded into a suitable pre-coated casting container (conveniently a sterile Petri dish or similar) via a 16 G needle or equivalent. It is useful to pre-coat the casting dish with serum containing media or albumin to prevent the gel from adhering. The gel set within a few minutes. The gel was then bathed in 20 ml of medium (Table 2) and the casting dish covered with a lid. The set gel was incubated at 37° C. for 16-24 hours to allow development (or maturation) of the cells.

Packing and Storage

After development (or maturation), the set gels were removed from their casting containers and placed into pre-irradiated, sterile foil pouches, stored within a sterile roto-seal bag. 10 ml serum-free medium (as per Table 2, without the foetal bovine serum) was added to each pouch before sealing. The shelf life of the sealed units is up to 28 days at 4° C.

EXAMPLE 2

Low Protein Concentration Product

For certain applications, it is possible to use lower protein concentrations. The chief advantage of this is reduction of production costs, since serum-derived proteins and many protease inhibitors, such as aprotinin, are expensive. In a preferred embodiment, the concentration of fibrin in the set product is reduced to less than 7 mg.ml$^{-1}$. In practice, 3.0-4.0 mg.ml$^{-1}$ is found to be effective.

One important consideration is the effectiveness (as well as the cost) of using aprotinin as protease inhibitor in such 'low protein' products. In particular, pro rata dilution of commercial products results in aprotinin concentrations that are too low to be effective. A preferable solution is to use an alternative inhibitor, such as tranexamic acid. Not only is this a highly effective inhibitor of fibrinolysis, but it has significant cost advantages.

Matrix

In this embodiment the matrix protein is fibrin, sourced from a commercial fibrin sealant, Tisseel®, using tranexamic acid instead of aprotinin. The key components of the matrix are summarised in Table 3. It should be noted that the same matrix composition could also be achieved using another commercially available fibrin sealant, Quixil. However the addition of exogenous tranexamic acid should be reduced as it already contains this inhibitor.

TABLE 3

Components of the Fibrinogen Matrix in Example 2

| Component | Final concentration in cellularised scaffolds |
|---|---|
| Matrix protein (fibrinogen) | 3.5 mg/ml |
| Tranexamic acid | 10 mg/ml |
| Thrombin | 25 IU/ml |
| Calcium chloride | 4 mM |

Freeze-dried Tisseel® fibrinogen is reconstituted with supplemented L-15 medium solution before being added to the working cell suspension in supplemented L-15 medium. Once reconstituted, Tisseel® fibrinogen should be used within 4 hours, ideally within 1-2 hours.

Tisseel® thrombin powder is reconstituted in a calcium chloride solution according to the manufacturer's directions. Once dissolved, the thrombin/CaCl$_2$ solution is further diluted with supplemented L-15 medium containing tranexamic acid to obtain a working thrombin solution.

The cell density used is again in the range 450 to 2500 cells mm$^2$. In order to minimise costs, it may be desirable to use a cell density of approximately 450 to 550 cells mm$^{-2}$. It should be noted, however, that protein concentration and cells density are independent variables. Lowering protein concentration is the major cost determinant, rather than cell density. However, being able to use fewer cells may have implications for the speed of production. In any case, high cell density/low protein concentration and low cell density/high protein concentration embodiments are envisaged and may be preferred in specific circumstances.

EXAMPLE 3

Packaging, Storage and Delivery

A major factor contributing to the success of topical wound healing compositions is the ease of accurately applying them to the wound surface so that a close contact is established, without air bubbles or creases, under sterile operating conditions. Wound healing compositions may be fragile, and handling should be kept to a minimum. The composition of the invention is preferably packaged in such a way as to significantly assist and facilitate application. In addition, the composition is shipped and stored chilled, rather than frozen, so that detailed thawing procedures are not required prior to use.

After setting and the 16-24 hour culture and development (or maturation) period, the individual gel discs are packaged by insertion into a flexible foil or metalised plastic pouch comprising two rectangular sheets, sealed along a substantial portion of three of their sides so as to form an open pocket. The inner surface of one of these sheets is modified so as to increase its adherence to the gel product. In a preferred embodiment as shown in FIG. 2, the packaging used is an Oliver® Products Company (Grand Rapids, Mich. USA) peelable foil pouch comprising one foil sheet and one sheet of laminated polyester/foil sheet with Q15 Adhesive dot pattern coating. Q15/48BF1 is a laminated lidding and pouching material for medical devices. The purpose of this dot pattern adhesive coating is to improve the efficiency of the heat sealing process which is used to seal the edges of the sheets together. However, the adhesive and raised dot pattern prove highly effective in providing a surface to which composition preferentially adheres, as compared with the smooth, uncoated inner surface of the opposing sheet. Other forms of coating and/or roughening of the surface of one of the internal surfaces of the pouch could be used to achieve the same effect. Similarly, any suitably durable, flexible, water and gas-impermeable sheet material might be used to manufacture such a pouch. All or part of the packaging might be transparent to allow visual inspection, for example, of the integrity of the composition or of the colour of a pH indicator dye in the cell culture medium, a small volume of which is inserted in the pouch, along with the composition, before the pouch is sealed along its remaining open edge.

Thus sealed, the composition has a shelf-life of at least 7-11 days, and preferably up to 28 days, more preferably 21 days, at 2° to 8° C.

For application, as shown in FIG. 2, the pouch is peeled apart, under sterile conditions, leaving the composition adhering to the treated inner surface of one of the sheets comprising the pouch. Using the sheet as a backing or means of support the composition is then applied to the surface of the wound, to which, in the absence of excessive exudation, it will preferentially adhere allowing it to be peeled away from the sheet. This means of application allows the composition to be applied without wrinkling or incorporation of air bubbles, and with the minimum of manipulation. The edges of the composition may be easily trimmed to fit the limits of the wound. Another advantage of delivering the composition in a format that is reversibly adherent to the packaging, as described, is that it allows the easy identification of the orientation of the product and facilitates oriented application, should this be required. In the case of a homogenous wound-healing product, orientation of the product on the wound is not important. However, where a multilayered composition is involved, such as one with a fibroblast layer that is intended to be applied in contact with the wound surface and a keratinocyte layer that is intended to be oriented away from the wound surface, it may be difficult or impossible to establish the orientation visually. In this case, the ability to deliver the product in such a way as makes incorrect application impossible without first removing the composition from the packaging offers a significant advantage.

EXAMPLE 4

Genetic Expression Profile of Wound Healing Composition

By way of example, human dermal fibroblasts (HDFs) obtained from human neonatal foreskin and of the same passage number and origin were seeded into a matrix, as specified below, or seeded without exogenous matrix, into tissue culture-appropriate containers:
(i) HDFs+Collagen;
(ii) HDFs+Fibrin;
(iii) HDFs (no exogenous matrix applied); and
(iv) Wound healing composition comprising HDFs and fibrin manufactured to production specifications (see Examples 1 and 3 above).

After a 24 h period of maturation at 37° C., which began on day 0, the fibroblasts were examined to profile gene expression in the constructs under different storage or incubation conditions. Constructs (i), (ii) and (iii) were examined on day 1, 5, 14, and 21 each in duplicate. Construct (iv) was examined 9 days after storage in a sealed, sterile package as described in Example 3 above.

RNA Extraction

Total RNA was extracted from samples using TriReagent (Sigma) following the manufacturers protocol for total RNA extraction. The integrity of RNA was tested by electrophoresis of a sample of the isolated RNA through a 2% agarose (InVitrogen) gel and staining with ethidium bromide (Sigma) to visualise the RNA in the gel.

Differential Display

In order to quickly visualise and, by way of example, identify differences in gene expression between samples cast in different or no matrix, an aliquot of each RNA sample was processed by conversion to polyA cDNA products for analysis by differential display techniques. Briefly, polyA cDNA products were amplified using a collection of proprietary primers (Epistem Ltd. UK) designed to prime DNA synthesis at random and reveal differences in gene expression between two samples. In the illustration shown in FIG. 3a, two proprietary primers A and B indicated by broken grey lines, have annealed to homologous complementary sequences on a single cDNA molecule, representing gene Y, to prime synthesis of a PCR product, "AB", of relatively small size. In the illustration, the arrows indicate the direction of DNA synthesis from the primers. Conversely, in FIG. 3b, a second pair of proprietary primers C and D have annealed to homologous complementary sequences on a second cDNA, representing gene Z, at sites which are a relatively greater distance from each other, resulting in a PCR product, "CD", of relatively larger size.

Electrophoresis reveals the PCR products AB and CD as bands migrating through the electrophoresis medium closer or farther from the migration origin of the medium (i.e. the top of the gel), as depicted in FIG. 3c. Here, cDNA products AB and CD from three different samples (s1, s2 and s3), are illustrated. In sample 1, electrophoresis reveals product AB as a more intense band (relatively high abundance) that has moved to the bottom of the gel (small product size) whereas in sample 2, the same product yields a band of identical size but of relatively less intensity, signifying that more of product AB was present in sample 1 than in sample 2. Similarly, product CD, migrating proximal to the origin of electrophoresis (larger size) produces a relatively more intense band in samples 1 and 2 than in sample 3, indicating its relative paucity in sample 3 compared to samples 1 and 2. Products sharing the same position after electrophoresis may represent a single identical product expressed in all samples whilst those present in only some samples may be expressed specifically under the conditions present when that sample was collected. PolyA cDNA products from different samples will thus produce a characteristic pattern of large/small, abundant/rare, products similar to a "bar code" for that sample.

Using the differential display technique, patterns shown in FIG. 4, FIG. 5 and FIG. 6 were obtained. Where a difference in gene expression from young samples (i.e. samples kept up to 14 days in storage) compared with older samples (i.e. samples older than 14 days in storage) was noted, the appropriate differentially-expressed bands were excised. DNA sequences corresponding to the excised differentially-expressed bands were obtained using by proprietary DNA sequencing techniques (Epistem Ltd, UK). The DNA sequences were searched against the Genbank database and corresponding "differentially-expressed genes" (which includes cDNAs or Genbank accession numbers of unknown genes) identified.

The differentially-expressed genes (i.e. DD2, DD4, DD5, DD10, DD12, DD13, GB1 and GB5) were then, together with a selection of genes known or suspected to respond to components within the samples (for example, fibrin or serum), analysed further by semi-quantitative PCR, as described below.

Semi-Quantitative PCR

In order to analyse gene expression, an aliquot of RNA ($10^{-4}$ to 1500 ng RNA) isolated as above was subjected to reverse transcription and PCR amplification as described in Brady & Iscove (1993, Methods Enzymol 225: 611-623) using the primer NotIdT (5'CAT CTC GAG CGG CCG CTT TTT TTT TTT TTT TTT TTT TTT T 3'; SEQ ID NO: 1) to produce polyA cDNA. The relative quantities of the resulting products were estimated by electrophoresis of a small sample (1 µl) the PCR products (polyA cDNA) through a 2% agarose gel using dilutions of a known concentration of maximally sheared (100-800 bp) diploid human genomic DNA as standards. Using electronic gel documentation (Syngene), the amount of polyA cDNA representing each RNA sample, was estimated relative to the genomic standard and this information was further used to normalise gene expression data yielded by TaqMan® Realtime/Q-PCR analyses (see below).

PolyA cDNA products were diluted (typically 1000-fold) and aliquots from each sample processed for TaqMan® quantitative PCR using primers to specific genes (see Table 3 below) to amplify corresponding template, if any was present, in the polyA cDNA collections. In order to detect specific amplification products resulting from amplification in TaqMan® real-time PCR, synthesised products were labelled fluorescently by inclusion of SYBR-Green (Molecular Probes) in the reaction mixture. As cDNA is synthesised in the real-time PCR reaction, the fluorescent signal is incorporated into the PCR product and is detected by the instrument (ABI 7700 or equivalent, Applied Biosystems Inc.). The amount of fluorescent signal is directly proportional to the amount of starting template in the reaction. The point at which the fluorescent signal is detectable by the instrument is called the "threshold cycle" and is called the Ct value.

The standard TaqMan® reaction is 40 cycles as indicated in the manufacturer's instructions. The first cycle at which SYBR-green labelled PCR product can be detected by the instrument is called the "threshold" cycle (Ct) for the gene under investigation. If there were no template to amplify, no fluorescence would be incorporated since no product is made, and the Ct value would be 40 (i.e. fluorescence was not detectable after 40 cycles). In a standard reaction of 40 cycles, a reaction that produced no fluorescent signal upon completion of 40 cycles would be equivalent to a product in which no template for amplification had been included. A Ct value less than 40 indicates that the primers recognised a target template and that DNA was synthesised incorporating the fluorescent SYBR-Green "tag".

TABLE 3

PCR primers for amplification of specific human genes by TaqMan [RTM] real-time PCR

| Primer Abbreviation | Gene Name/ Designation | 5' to 3' sequence |
|---|---|---|
| HsAPOD_54F | Apolipoprotein D | GGTAACAGGGTAGGGCATGGT [SEQ ID NO: 2] |
| HsAPOD_136R | | CCACCCCCCCCCATAAA [SEQ ID NO: 3] |
| HsMMP2_520F | Matrix metalloprotease 2 | GGGCTGAGCGGGAAGC [SEQ ID NO: 4] |
| HsMMP2_606R | | CCCCTGTTCACTCTACTTAGCATGT [SEQ ID NO: 5] |
| HsCol3A1_299F | Collagen 3a1 | CATTAGCACCATAACATGCGTCTT [SEQ ID NO: 6] |
| HsCol3A1_382R | | GGTGCTCCTCTTTTTTCTTGTCA [SEQ ID NO: 7] |
| HsGas6_103F | Growth arrest specific 6 | GGGCCCACGGCTGAGT [SEQ ID NO: 8] |
| HsGas6_173R | | GGCCTGTAACATATCTGTAAATAGTGAGA [SEQ ID NO: 9] |
| HsPAI_70F | Plasminogen activator inhibitor | GCACTCAAGGGCAAGGATATG [SEQ ID NO: 10] |
| HsPAI_150R | | GCGTGCCCAGCTCTTCAC [SEQ ID NO: 11] |
| HsPLAU_196F | Urokinase | AAACTGAGACAGTGCTGGTCACA [SEQ ID NO: 12] |
| HsPLAU_268R | | GGGTCCCCCACGTGACA [SEQ ID NO: 13] |
| HsVIM_174F | Vimentin | TTGTAGGAGTGTCGGTTGTTAAGAAC [SEQ ID NO: 14] |
| HsVIM_261R | | TCAAGTGCCTTTCTGCAGTTTTT [SEQ ID NO: 15] |
| HsSMActin_194F | Smooth muscle actin | GGCCCGGCTTCATCGTAT [SEQ ID NO: 16] |
| HsSMActin_267R | | GGCTCCATCCTGGCCTCT [SEQ ID NO: 17] |
| HsPDGFb_109F | Platelet derived growth factor | CCCCAAAAATATAATCACCGACTT [SEQ ID NO: 18] |

TABLE 3-continued

PCR primers for amplification of specific human genes by TaqMan [RTM] real-time PCR

| Primer Abbreviation | Gene Name/ Designation | 5' to 3' sequence |
|---|---|---|
| HsPDGFb_200R | | CACCTCCCTTCCCACCTACTG [SEQ ID NO: 19] |
| HsCOX2_154F | Cyclo-oxygenase 2 | AAACGAAGTGTTTGAGAAGAC-TGTGT [SEQ ID NO: 20] |
| HsCOX2_262R | | AATTCAGTAGGTGCATTGGAA-TCA [SEQ ID NO: 21] |
| HsGAPDH_F | Glyceralde-hyde 3-phosphate dehydroge-nase | ACACTCAGACCCCCACCACA [SEQ ID NO: 22] |
| HsGAPDH_R | | CATAGGCCCCTCCCCTCTT [SEQ ID NO: 23] |
| HsRPL32_402TF | Ribosomal protein L32 | CTGGCCATCAGAGTCACCAA [SEQ ID NO: 24] |
| HsRPL32_466R | | TGAGCTGCCTACTCATTTTCTT-CA [SEQ ID NO: 25] |
| HsCol6A1_276F | Collagen 6a | CACCGTTAATCTCGAGGGTCTT [SEQ ID NO: 26] |
| HsCol6A1_342R | | TGACCCCGACCTCAGAGAGTAC [SEQ ID NO: 27] |
| HsINSIG1_194F | Insulin in-duced gene 1 | AATGAAATCGAATACTTGGGA-AGCT [SEQ ID NO: 28] |
| HsINSIG1_268R | | TCTGTGCCCTGGAGCATTCT [SEQ ID NO: 29] |
| HsCol1A1_231F | Collagen 1a1 | GGATGGAGGGAGTTTACAGGAA [SEQ D NO: 30] |
| HsCol1A1_296R | | GTGCCCCAGACCAGGAATT [SEQ ID NO: 31] |
| DD2_42F | gi|7022020 | TCCCTGTGCCCAGAGTAACC [SEQ ID NO: 32] |
| DD2_114R | | AGGTCTGGCTCCTGTGTTTTACA [SEQ ID NO: 33] |
| DD4_386F | gi|46267369 | TTATTGAAAGCTGACCTGCTAA-TGA [SEQ ID NO: 34] |
| DD4_459R | | GGGCAGTCACCCATTCAATT [SEQ ID NO: 35] |
| DD5_116F | X-ray re-pair, com- | CCCATAGAGCTGGTGAGGAAGT [SEQ D NO: 36] |
| DD5_182R | plementing defective, in chinese hamster, 1 (XRCC1) | CGTTCGTCCCCGATGGA [SEQ ID NO: 37] |
| DD10_98F | gi|10437022 | GTCCACAGTGCCCCTTCCT [SEQ ID NO: 38] |
| DD10_169R | | CGCTCCCTGGCATCATG [SEQ ID NO: 39] |
| DD12_154F | Ribosomal protein S8 | AAGCGATGCACGCAAGAAG [SEQ ID NO: 40] |
| DD12_223R | | AAGAATGCCAAAATCAGCAGT-CT [SEQ ID NO: 41] |
| DD13_77F | Huntingtin Interacting Protein K | GGCAATAAGCGCCTCTACCA [SEQ ID NO: 42] |
| DD13_142R | | CCTCGAGCAGCAGCAGAAC [SEQ ID NO: 43] |
| GB1_74F | gi|24810897 | TCAGGGCAACACCACACACT [SEQ ID NO: 44] |
| GB1_156R | | CCATGTTTGAGCTTCTGTTTCAA [SEQ ID NO: 45] |
| GB5_278F | Ribosomal protein S24 | TCATGCCAAAGCCAGTTGTC [SEQ ID NO: 46] |
| GB5_351R | | CACACCGGATGTCATCTTTGTA-TT [SEQ ID NO: 47] |

Table 4 below shows the level of expression of selected genes in fibroblast-containing products. The second column gives the actual gene name if known or the accession number. The values are expressed as fold level increases compared to RPL32 (a "house-keeping" gene). Expression levels for the columns labelled "Range for young cells" and "Preferred range for young cells" are pooled from fibroblasts in fibrin, collagen and grown on cell culture plastic and from days 1 to 14. This generates a range of expression from the largest value seen to the lowest value seen (column labelled "Range for young cells"). The column labelled "Preferred range for young cells" is a narrower range centred around the mean. The column labelled "Mean range for old cells" is the mean value of gene expression for all samples at day 21 in all matrices. Where the term "None" is given in a column, this indicates that there was no apparent increase or decrease in gene expression detected, i.e. no correlation between gene expression in young versus old cells could be observed.

TABLE 4

Ranges of fold change in gene expression compared to RPL32

| Gene acronym | Gene name or accession number | Range for young cells | Preferred range for young cells | Mean range for old cells |
|---|---|---|---|---|
| APOD | Apolipoprotein D | 2-48,000 | 100-2,000 | 15,000 |
| MMP2 | Matrix metalloprotease 2 | 2,000-1.6 × $10^6$ | 13,000-100,000 | 290,000 |
| Coll3a11 | Collagen 3a1 | 20-44,000 | 800-1,900 | 23,000 |
| Gas6 | Growth arrest specific 6 | None | None | None |
| PAI | Plasminogen activator inhibitor | None | None | None |

TABLE 4-continued

Ranges of fold change in gene expression compared to RPL32

| Gene acronym | Gene name or accession number | Range for young cells | Preferred range for young cells | Mean range for old cells |
|---|---|---|---|---|
| PLAU | Urokinase | — | 130-760 | 1400 |
| Vim | Vimentin | — | 28,000-2,065,000 | 4,800,000 |
| SMA | Smooth muscle actin | 20-150,000 | 1,600-8,600 | 22,000 |
| PDGF | Platelet derived growth factor beta | None | None | None |
| Cox2 | Cyclo-oxygenase 2 | None | None | None |
| GAPDH | Glyceraldehyde 3-phosphate dehydrogenase | None | None | None |
| Coll6a | Collagen 6a | None | None | None |
| INSIG1 | Insulin induced gene 1 | None | None | None |
| Coll1a1 | Collagen 1a1 | None | None | None |
| DD2 | gi\|7022020 | 0-750,000 | 0-4 (0-13 d) 0-136,000 (+cold) | $0.0575\text{-}3.14 \times 10^6$ |
| DD4 | gi\|46267369 | — | 0.3-1.6 | 5.00 |
| DD5 | X-ray repair, complementing defective, in chinese hamster, 1 | 0.6-500 | 13-160 | 560.00 |
| DD10 | gi\|10437022 | 0-210 | 3-15 | 94.00 |
| DD12 | Ribosomal protein S8 | 120-36,000 | 1,000-30,000 | 1,190-609,000 |
| GB1 | gi\|24810897 | 0-33 | 0-5 | 36.00 |
| GB5 | Ribosomal protein S24 | 1,000-120,000 | 11,000-53,000 | 100,000.00 |

The effects of maturation and/or manipulation over time and of storage and/or shipping conditions on gene expression in products of the invention are summarised in Table 5. HDFs cast in fibrin, collagen, or cast onto tissue-culture appropriate plastic, were analysed for gene expression over 21 (31) days after casting. In addition, HDFs cast in fibrin were stored at 4° C. (±4° C.) and assayed over a period of 22 (30) days (Cold).

TABLE 5

Gene expression summary

| Young Profile (d1-d5) | Older Young Profile (d1-d14) | Other |
|---|---|---|
| Box 2 (4° C. and 37° C.) | Box1 (4° C. and 37° C.) | Box 3 (4° C.) |
| √DD5 | √ApoD | √GB5 |
| √DD10 | √MMP2 | √Gas6 |
| √GB1 | √Coll3a11 | √GAPDH |
|  | √SMA | √PAI |
|  |  | √PLAU |
|  |  | √Vimentin |
| Box 5 (37° C.) | Box 4 (37° C.) | Box 6 (4° C. and 37° C.) |
| √GB5 | √DD2 | √RPL32 |
| √DD12 |  |  |

Box 1 shows genes whose range of expression is characteristic of young cells subjected to a minimum of further manipulation after casting (up to 14 days) at maturation temperature (37° C.) or storage temperature (4° C.).

Box 2 shows genes whose range of expression is characteristic of young cells subjected to no further manipulation after casting (up to 5 days) at maturation temperature (37° C.) or storage temperature (4° C.).

Box 3 shows genes whose range of expression is unrelated to age but whose range of expression is dependent on and differs under storage temperature (4° C.) relative to maturation conditions (37° C.).

Box 4 shows genes whose range of expression is specific to young cells subjected to a minimum of further manipulation after casting (up to 14 days) at 37° C. and which is different at storage temperature.

Box 5 shows genes whose range of expression specifically in young cells subjected to no further manipulation after casting (up to 5 days) at 37° C. and which is different at storage temperature.

Box 6 shows genes whose range of expression is unrelated to age or temperature under circumstances investigated.

The genes indicated in Box 1 and Box 2 can therefore be nominated as genes which are indicative of a young phenotype of a wound healing composition.

EXAMPLE 5

Gene Expression Specific to Fibroblasts in a Fibrin Matrix

In Example 5, the level of gene expression of various genes over time in a wound healing composition comprising fibroblasts in a fibrin matrix, another embodiment comprising fibroblasts in a collagen matrix, and a further embodiment comprising fibroblasts in a liquid culture medium were determined. The inventors were able to identify that specific genes had significantly higher expression levels in the fibrin matrix than the other embodiments.

The data was generated by TaqMan® quantitative PCR. The samples were of three types. Human dermal fibroblasts were either embedded in a fibrin matrix at 1500 cells/mm$^2$, as described in Example 2 above, or were embedded in a rat tail collagen matrix at 1500 cells/mm$^2$, or were plated onto cell culture plastic. The samples were collected for PCR on the day following manufacture (d1) or on day 5, day 14 or day 21. Each sample was manufactured in duplicate and each Taqman® run was conducted in duplicate. The starting material was normalised for quantity of cDNA. Analysis was based on a two-way analysis of variance model using the statistical software program R (v1.8.1).

TABLE 6

Ranges of expression of human dermal fibroblasts in fibrin.

| 1 Gene | 2 <14 d or at 4deg | 3 mean | 4 21 d | 5 mean |
|---|---|---|---|---|
| APOD | 2.08-48,200 | 4,360 | 323-190,000 | 50,000 |
| MMP2 | 694-662,000 | 102,000 | 10,900-3,840,000 | 1,750,000 |
| Coll3a1 | 33.7-43,300 | 4,370 | 999-259,000 | 106,000 |
| Gas6 | 0.0136-7.09 | 1.44 | 0.448-4.52 | 1.75 |
| SMA | 20.2-121,000 | 14,100 | 635-237,000 | 106,000 |
| Coll6a | 10.3-2,860 | 832 | 505-6,790 | 3,660 |
| Coll1a | 30.4-16,600 | 5,730 | 1,390-48,000 | 23,500 |
| DD5 | 0.0371-1,220 | 148 | 55.2-491 | 302 |
| DD4 | 0.0000233-4.28 | 0.279 | 0-0.265 | 0.112 |
| GB1 | 0.00161 | 9.73 | 3.57-21.9 | 14.4 |
| PAI | 12.2-11,500 | 2,330 | 40.5-8,080 | 2,770 |
| PLAU | 3.71-7,800 | 752 | 61.4-14,500 | 6,480 |
| INSIG1 | 0.842-85.2 | 19.2 | 22.2-81.1 | 49.4 |
| DD2 | 0.0000233-740,000 | 24,000 | 0.00026-11.8 | 3.26 |
| DD10 | 0.0000233-38.7 | 2.26 | 16.3-126 | 53.4 |
| DD12 | 105-37,800 | 8,390 | 3,230-19,700 | 13,100 |
| GB5 | 1,220-292,000 | 45,700 | 14,400-67,200 | 50,600 |

Values in Table 6 are expressed to 3 significant figures.

The above expression levels were determined for human dermal fibroblasts cast in fibrin under the following conditions: stored at 4° C. and harvested 6, 9, 20 and 23 days later or stored at 37° C. and harvested 1.5 and 14 days later (columns 2 and 3). Table 6 also shows the expression levels of these genes in constructs where the cells were cast in fibrin and stored at 37° C. and harvested 21 days later.

Statistical Analysis

Gene activity was determined in the "Protoderm" (Pd) gel compared to a collagen control (Calloderm, Cd) and negative control (Cells alone, HDF) treatment. One batch of cells was tested. There were 4 time points (0, 4, 13 and 20 days), with 2 replicate cultures. All time points and replicate cultures were considered independent, but no replication of cell batch. Two replicate aliquots of each culture were assayed on the TaqMan®; these were very close and the mean of the two values were used in the analysis.

Data were expressed as a corrected ct value and analysed as such.

The main analysis was based on a standard 2-way analysis of variance model, with time treated as a factor (i.e. no account of the ordering) and the effect of the gel tested after allowing for time. In this model we assumed the same time-trend for each gel—that is we assume the lines are parallel (on the Ct scale). We then tested if the average difference over the time points differs between the gels as the main test for a gel effect. Additionally we tested for a time by gel interaction to see if there is any evidence for a difference in the time course between the gels. If there was a significant interaction then we had evidence for a differential effect at the different time points.

There are two specific differences we pre-specified as of interest, the overall difference between Protoderm and each of the controls. Specific contrasts have been determined for these differences (as Δct values), along with their 95% confidence intervals and associated P-values. One other contrast between the controls as a secondary endpoint of interest has also been determined.

Statistical results for each gene tested are given in Table 7 below. The first block gives the ANOVA model followed by a formal ANOVA table. The third block gives the effect sizes for the comparisons of interest on the Δct scale along with the their associated SEs and P-values (labelled Pr(>|t|)), and the 95% confidence intervals ("lower CI" to "upper CI"). The P-values are the most useful parameters here. The fourth block gives the same comparisons but expressed as ratios, so may be more meaningful, giving the average fold difference between the pairs of gels. Inverting might be an idea where the ratios are less than one. The CIs give the range of values of this fold-difference that are loosely compatible with the data. The CIs are generally wide and asymmetric, reflecting the log-scale analysis. The 5$^{th}$ block gives the results of formal (likelihood-ratio) tests. Firstly an overall test for any difference between the 3 gels, secondly a test for any time effects and finally a formal test for an interaction—that is for the time course being different between gels. Either of the gel test or the interaction test being significant (P<0.05) is evidence for gel differences.

TABLE 7

Statistical analysis data

-- Coll6a --
Pooled time effects model

| | Estimate | Std. Error | t value | Pr(>|t|) |
|---|---|---|---|---|
| (Intercept) | 21.30466679 | 0.5926364 | 35.9489673 | 3.250935e-18 |
| as.factor(time)4 | 0.22052495 | 0.6843176 | 0.3222553 | 7.509720e-01 |
| as.factor(time)13 | 0.09941046 | 0.6843176 | 0.1452695 | 8.861124e-01 |
| as.factor(time)20 | 0.63034869 | 0.6843176 | 0.9211347 | 3.691617e-01 |
| gelhdf | -0.42598809 | 0.5926364 | -0.7188018 | 4.814909e-01 |
| gelpd | 1.50800994 | 0.5926364 | 2.5445786 | 2.032882e-02 |

TABLE 7-continued

Analysis of Variance Table

Response: Col6a

|  | Df | Sum Sq | Mean Sq | F value | Pr(>F) |
|---|---|---|---|---|---|
| as.factor(time) | 3 | 1.3806 | 0.4602 | 0.3276 | 0.80545 |
| gel | 2 | 16.5224 | 8.2612 | 5.8804 | 0.01083* |
| Residuals | 18 | 25.2877 | 1.4049 |  |  |

---
Signif. codes:
0 '***'
0.001 '**'
0.01 '*'
0.05 '.'
0.1 ' ' 1

Ct-scale effects . . .

|  | Estimate | Std. Error | t value | Pr(>|t|) | DF | lower CI | upper CI |
|---|---|---|---|---|---|---|---|
| gel: pd v hdf | 1.9339980 | 0.5926364 | 3.2633804 | 0.004316248 | 18 | 0.6889151 | 3.1790809 |
| gel: pd v cd | 1.5080099 | 0.5926364 | 2.5445786 | 0.020328822 | 18 | 0.2629271 | 2.7530928 |
| gel: hdf v cd | −0.4259881 | 0.5926364 | −0.7188018 | 0.481490899 | 18 | −1.6710710 | 0.8190948 | ratio scale (fold increases) . . .

|  | Estimate | lower CI | upper CI |
|---|---|---|---|
| gel: pd/hdf | 3.8211265 | 1.6120708 | 9.057299 |
| gel: pd/cd | 2.8441744 | 1.1999107 | 6.741608 |
| gel: hdf/cd | 0.7443288 | 0.3140201 | 1.764299 |

Pooled gel effects: P = 0.01083055
Pooled time effects: P = 0.8054453
Interaction: P = 0.9089068

-- APOD --
Pooled time effects model

|  | Estimate | Std. Error | t value | Pr(>|t|) |
|---|---|---|---|---|
| (Intercept) | 17.8298122 | 0.5333194 | 33.431772 | 5.965467e−17 |
| as.factor(time)4 | 2.9121916 | 0.6129928 | 4.750776 | 1.851666e−04 |
| as.factor(time)13 | 3.2827438 | 0.6129928 | 5.355273 | 5.247162e−05 |
| as.factor(time)20 | 4.5197668 | 0.6461511 | 6.994907 | 2.158380e−06 |
| gelhdf | 0.8015119 | 0.5308673 | 1.509816 | 1.494529e−01 |
| gelpad | 2.9150736 | 0.5525442 | 5.275729 | 6.179920e−05 |

Analysis of Variance Table

Response: APOD

|  | Df | Sum Sq | Mean Sq | F value | Pr(>F) |
|---|---|---|---|---|---|
| as.factor(time) | 3 | 56.368 | 18.789 | 16.668 | 2.61e−05*** |
| gel | 2 | 32.914 | 16.457 | 14.599 | 0.0002039*** |
| Residuals | 17 | 19.164 | 1.127 |  |  |

---
Signif. codes:
0 '***'
0.001 '**'
0.01 '*'
0.05 '.'
0.1 ' ' 1

Ct-scale effects . . .

|  | Estimate | Std. Error | t value | Pr(>|t|) | DF | lower CI | upper CI |
|---|---|---|---|---|---|---|---|
| gel: pd v hdf | 2.1135616 | 0.5525442 | 3.825145 | 0.0013548358 | 17 | 0.9477952 | 3.279328 |
| gel: pd v cd | 2.9150736 | 0.5525442 | 5.275729 | 0.0000617992 | 17 | 1.7493071 | 4.080840 |
| gel: hdf v cd | 0.8015119 | 0.5308673 | 1.509816 | 0.1494529182 | 17 | −0.3185203 | 1.921544 |

TABLE 7-continued

|  | ratio scale (fold increases) . . . | | |
|---|---|---|---|
|  | Estimate | lower CI | upper CI |
| gel: pd/hdf | 4.327583 | 1.928923 | 9.709036 |
| gel: pd/cd | 7.542661 | 3.361971 | 16.922139 |
| gel: hdf/cd | 1.742927 | 0.801892 | 3.788283 |

Pooled gel effects: P = 0.0002039492  
Pooled time effects: P = 1.425922e−05  
Interaction: P = 0.0002168541

-- MMP2 --  
Pooled time effects model

|  | Estimate | Std. Error | t value | Pr(>|t|) |
|---|---|---|---|---|
| (Intercept) | 26.6152636 | 0.3650609 | 72.9063574 | 1.150719e−22 |
| as.factor(time)4 | 0.5463583 | 0.4195980 | 1.3020995 | 2.102493e−01 |
| as.factor(time)13 | 0.3485771 | 0.4195980 | 0.8307408 | 4.176353e−01 |
| as.factor(time)20 | 1.4279613 | 0.4422951 | 3.2285262 | 4.934995e−03 |
| gelhdf | 0.4746369 | 0.3633825 | 1.3061634 | 2.088947e−01 |
| gelpd | 1.0305944 | 0.3782205 | 2.7248508 | 1.440711e−02 |

Analysis of Variance Table

Response: MMP2

|  | Df | Sum sq | Mean Sq | F value | Pr(>F) |
|---|---|---|---|---|---|
| as.factor(time) | 3 | 5.0204 | 1.6735 | 3.1683 | 0.05127. |
| gel | 2 | 3.9217 | 1.9608 | 3.7124 | 0.04595* |
| Residuals | 17 | 8.9792 | 0.5282 |  |  |

---
Signif. codes:  
0 '***'  
0.001 '**'  
0.01 '*'  
0.05 '.'  
0.1 ' ' 1

Ct-scale effects . . .

|  | Estimate | Std. Error | t value | Pr(>|t|) | DF | lower CI | upper CI |
|---|---|---|---|---|---|---|---|
| gel: pd v hdf | 0.5559575 | 0.3782205 | 1.469930 | 0.15984572 | 17 | −0.2420180 | 1.353933 |
| gel: pd v cd | 1.0305944 | 0.3782205 | 2.724851 | 0.01440711 | 17 | 0.2326189 | 1.828570 |
| gel: hdf v cd | 0.4746369 | 0.3633825 | 1.306163 | 0.20889471 | 17 | −0.2920331 | 1.241307 |

|  | ratio scale (fold increases) . . . | | |
|---|---|---|---|
|  | Estimate | lower CI | upper CI |
| gel: pd/hdf | 1.470144 | 0.8455617 | 2.556080 |
| gel: pd/cd | 2.042866 | 1.1749659 | 3.551848 |
| gel: hdf/cd | 1.389568 | 0.8167502 | 2.364126 |

Pooled gel effects: P = 0.04594612  
Pooled time effects: P = 0.03277902  
Interaction: P = 0.0003007804

-- INSIG1 --  
Pooled time effects model

|  | Estimate | Std. Error | t value | Pr(>|t|) |
|---|---|---|---|---|
| (Intercept) | 19.0169997 | 0.3809482 | 49.9201689 | 6.993250e−20 |
| as.factor(time)4 | −0.3711417 | 0.4378587 | −0.8476290 | 4.084204e−01 |
| as.factor(time)13 | 0.2510771 | 0.4378587 | 0.5734205 | 5.738682e−01 |
| as.factor(time)20 | 0.3885168 | 0.4615436 | 0.8417772 | 4.115984e−01 |
| gelhdf | 1.2383869 | 0.3791967 | 3.2658164 | 4.553893e−03 |
| gelpd | 1.2416361 | 0.3946805 | 3.1459273 | 5.894312e−03 |

TABLE 7-continued

Analysis of Variance Table

Response: INSIG1

| | Df | Sum Sq | Mean Sq | F value | Pr(>F) |
|---|---|---|---|---|---|
| as.factor(time) | 3 | 1.6431 | 0.5477 | 0.9523 | 0.437606 |
| gel | 2 | 7.9941 | 3.9970 | 6.9494 | 0.006227** |
| Residuals | 17 | 9.7777 | 0.5752 | | |

---
Signif. codes:
0 '***'
0.001 '**'
0.01 '*'
0.05 '.'
0.1 ' ' 1

Ct-scale effects . . .

| | Estimate | Std. Error | t value | Pr(>|t|) | DF | lower CI | upper CI |
|---|---|---|---|---|---|---|---|
| gel: pdvhdf | 0.003249145 | 0.3946805 | 0.008232344 | 0.993527451 | 17 | −0.8294539 | 0.8359521 |
| gel: pdvcd | 1.241636057 | 0.3946805 | 3.145927278 | 0.005894312 | 17 | 0.4089331 | 2.0743391 |
| gel: hdfvcd | 1.238386911 | 0.3791967 | 3.265816430 | 0.004553893 | 17 | 0.4383517 | 2.0384221 | ratio scale (fold increases) . . .

| | Estimate | lower CI | upper CI |
|---|---|---|---|
| gel: pd/hdf | 1.002255 | 0.5627422 | 1.785035 |
| gel: pd/cd | 2.364665 | 1.3277035 | 4.211514 |
| gel: hdf/cd | 2.359346 | 1.3550553 | 4.107960 |

Pooled gel effects: P = 0.006227319
Pooled time effects: P = 0.3793723
Interaction: P = 0.01828761

-- Coll3a1 --
Pooled time effects model

| | Estimate | Std. Error | t value | Pr(>|t|) |
|---|---|---|---|---|
| (Intercept) | 17.6265418 | 0.9267273 | 19.0202034 | 2.288392e−13 |
| as.factor(time)4 | −0.7269750 | 1.0700925 | −0.6793572 | 5.055545e−01 |
| as.factor(time)13 | −0.9339229 | 1.0700925 | −0.8727497 | 3.942933e−01 |
| as.factor(time)20 | 1.3861820 | 1.0700925 | 1.2953852 | 2.115551e−01 |
| gelhdf | 2.6215119 | 0.9267273 | 2.8287846 | 1.112787e−02 |
| gelpd | 6.2573849 | 0.9267273 | 6.7521319 | 2.507169e−06 |

Analysis of Variance Table

Response: Coll3a1

| | Df | Sum Sq | Mean Sq | F value | Pr(>F) |
|---|---|---|---|---|---|
| as.factor(time) | 3 | 19.820 | 6.607 | 1.9232 | 0.1620 |
| gel | 2 | 157.991 | 78.996 | 22.9953 | 1.103e−05*** |
| Residuals | 18 | 61.835 | 3.435 | | |

---
Signif. codes:
0 '***'
0.001 '**'
0.01 '*'
0.05 '.'
0.1 ' ' 1

Ct-scale effects . . .

| | Estimate | Std. Error | t value | Pr(>|t|) | DF | lower CI | upper CI |
|---|---|---|---|---|---|---|---|
| gel: pd v hdf | 3.635873 | 0.9267273 | 3.923347 | 9.962159e−04 | 18 | 1.6888912 | 5.582855 |
| gel: pd v cd | 6.257385 | 0.9267273 | 6.752132 | 2.507169e−06 | 18 | 4.3104031 | 8.204367 |
| gel: hdf v cd | 2.621512 | 0.9267273 | 2.828785 | 1.112787e−02 | 18 | 0.6745301 | 4.568494 |

TABLE 7-continued

| | ratio scale (fold increases) . . . | | |
|---|---|---|---|
| | Estimate | lower CI | upper CI |
| gel: pd/hdf | 12.431022 | 3.224088 | 47.92993 |
| gel: pd/cd | 76.499846 | 19.840866 | 294.95821 |
| gel: hdf/cd | 6.153947 | 1.596077 | 23.72759 |

Pooled gel effects: P = 1.102566e−05
Pooled time effects: P = 0.1620176
Interaction: P = 0.1936387

-- RPL32 --
Pooled time effects model

| | Estimate | Std. Error | t value | Pr(>|t|) |
|---|---|---|---|---|
| (Intercept) | 8.1460391 | 0.2784725 | 29.252580 | 5.566187e−16 |
| as.factor(time)4 | −0.7628084 | 0.3200739 | −2.383226 | 2.909614e−02 |
| as.factor(time)13 | −0.9564229 | 0.3200739 | −2.988131 | 8.261049e−03 |
| as.factor(time)20 | −0.7284739 | 0.3373875 | −2.159161 | 4.542028e−02 |
| gelhdf | 0.6777619 | 0.2771922 | 2.445098 | 2.566787e−02 |
| gelpd | 1.4876430 | 0.2885107 | 5.156283 | 7.911979e−05 |

Analysis of Variance Table

Response: RPL32

| | Df | Sum Sq | Mean Sq | F value | Pr(>F) |
|---|---|---|---|---|---|
| as.factor(time) | 3 | 3.4408 | 1.1469 | 3.7318 | 0.0315333* |
| gel | 2 | 8.1718 | 4.0859 | 13.2943 | 0.0003343*** |
| Residuals | 17 | 5.2248 | 0.3073 | | |

---
Signif. codes:
0 '***'
0.001 '**'
0.01 '*'
0.05 '.'
0.1 ' ' 1

Ct-scale effects . . .

| | Estimate | Std. Error | t value | Pr(>|t|) | DF | lower CI | upper CI |
|---|---|---|---|---|---|---|---|
| gel: pd v hdf | 0.8098811 | 0.2885107 | 2.807109 | 1.212263e−02 | 17 | 0.20117663 | 1.418586 |
| gel: pd v cd | 1.4876430 | 0.2885107 | 5.156283 | 7.911979e−05 | 17 | 0.87893854 | 2.096347 |
| gel: hdf v cd | 0.6777619 | 0.2771922 | 2.445098 | 2.566787e−02 | 17 | 0.09293758 | 1.262586 |

| | ratio scale (fold increases) . . . | | |
|---|---|---|---|
| | Estimate | lower CI | upper CI |
| gel: pd/hdf | 1.753067 | 1.149636 | 2.673233 |
| gel: pd/cd | 2.804304 | 1.839022 | 4.276254 |
| gel: hdf/cd | 1.599656 | 1.066540 | 2.399255 |

Pooled gel effects: P = 0.000334309
Pooled time effects: P = 0.0408322
Interaction: P = 0.4660532

-- Gas6 --
Pooled time effects model

| | Estimate | Std. Error | t value | Pr(>|t|) |
|---|---|---|---|---|
| (Intercept) | 9.1242451 | 0.3866560 | 23.59783805 | 1.973084e−14 |
| as.factor(time)4 | −0.2111417 | 0.4444191 | −0.47509595 | 6.407652e−01 |
| as.factor(time)13 | −0.1772562 | 0.4444191 | −0.39884920 | 6.949697e−01 |
| as.factor(time)20 | 0.0428687 | 0.4684589 | 0.09151006 | 9.281570e−01 |
| gelhdf | 0.4371369 | 0.3848782 | 1.13577975 | 2.718080e−01 |
| gelpd | 1.1661499 | 0.4005940 | 2.91105215 | 9.731856e−03 |

TABLE 7-continued

Analysis of Variance Table

Response: Gas6

|  | Df | Sum Sq | Mean Sq | F value | Pr(>F) |
|---|---|---|---|---|---|
| as.factor(time) | 3 | 0.1626 | 0.0542 | 0.0915 | 0.96375 |
| gel | 2 | 5.0743 | 2.5372 | 4.2820 | 0.03119* |
| Residuals | 17 | 10.0729 | 0.5925 |  |  |

---
Signif. codes:
0 '***'
0.001 '**'
0.01 '*'
0.05 '.'
0.1 ' ' 1

Ct-scale effects . . .

|  | Estimate | Std. Error | t value | Pr(>|t|) | DF | lower CI | upper CI |
|---|---|---|---|---|---|---|---|
| gel: pd v hdf | 0.7290130 | 0.4005940 | 1.819830 | 0.086439590 | 17 | −0.1161664 | 1.574192 |
| gel: pd v cd | 1.1661499 | 0.4005940 | 2.911052 | 0.009731856 | 17 | 0.3209705 | 2.011329 |
| gel: hdf v cd | 0.4371369 | 0.3848782 | 1.135780 | 0.271807966 | 17 | −0.3748852 | 1.249159 | ratio scale (fold increases) . . .

|  | Estimate | lower CI | upper CI |
|---|---|---|---|
| gel: pd/hdf | 1.657505 | 0.9226361 | 2.977688 |
| gel: pd/cd | 2.244120 | 1.2491706 | 4.031535 |
| gel: hdf/cd | 1.353915 | 0.7711668 | 2.377028 |

Pooled gel effects:   P = 0.03118783
Pooled time effects:  P = 0.9274544
Interaction:          P = 0.005516476

-- PAI --

Pooled time effects model

|  | Estimate | Std. Error | t value | Pr(>|t|) |
|---|---|---|---|---|
| (Intercept) | 21.3267798 | 0.3992429 | 53.4180608 | 2.226778e−20 |
| as.factor(time)4 | −2.5253084 | 0.4588864 | −5.5031235 | 3.879012e−05 |
| as.factor(time)13 | −3.0730895 | 0.4588864 | −6.6968420 | 3.753022e−06 |
| as.factor(time)20 | −2.0222702 | 0.4837087 | −4.1807603 | 6.271352e−04 |
| gelhdf | 0.3527619 | 0.3974073 | 0.8876584 | 3.871111e−01 |
| gelpd | 1.7179208 | 0.4136346 | 4.1532329 | 6.655511e−04 |

Analysis of Variance Table

Response: PAI

|  | Df | Sum Sq | Mean Sq | F value | Pr(>F) |
|---|---|---|---|---|---|
| as.factor(time) | 3 | 32.754 | 10.918 | 17.2828 | 2.08e−05*** |
| gel | 2 | 11.904 | 5.952 | 9.4219 | 0.001763** |
| Residuals | 17 | 10.739 | 0.632 |  |  |

---
Signif. codes:
0 '***'
0.001 '**'
0.01 '*'
0.05 '.'
0.1 ' ' 1

Ct-scale effects . . .

|  | Estimate | Std. Error | t value | Pr(>|t|) | DF | lower CI | upper CI |
|---|---|---|---|---|---|---|---|
| gel: pd v hdf | 1.3651589 | 0.4136346 | 3.3003982 | 0.0042264624 | 17 | 0.4924662 | 2.237852 |
| gel: pd v cd | 1.7179208 | 0.4136346 | 4.1532329 | 0.0006655511 | 17 | 0.8452281 | 2.590613 |
| gel: hdf v cd | 0.3527619 | 0.3974073 | 0.8876584 | 0.3871111412 | 17 | −0.4856941 | 1.191218 |

TABLE 7-continued

| | ratio scale (fold increases) ... | | |
|---|---|---|---|
| | Estimate | lower CI | upper CI |
| gel: pd/hdf | 2.576047 | 1.4068477 | 4.716941 |
| gel: pd/cd | 3.289620 | 1.7965487 | 6.023548 |
| gel: hdf/cd | 1.277003 | 0.7141534 | 2.283454 |

Pooled gel effects: $P = 0.001763163$
Pooled time effects: $P = 2.254791e{-}05$
Interaction: $P = 0.0003068727$ -- PLAU --
Pooled time effects model

| | Estimate | Std. Error | t value | Pr(>|t|) |
|---|---|---|---|---|
| (Intercept) | 17.7530414 | 0.7789173 | 22.7919471 | 3.501385e−14 |
| as.factor(time)4 | −1.1736417 | 0.8952809 | −1.3109200 | 2.073180e−01 |
| as.factor(time)13 | −2.2389229 | 0.8952809 | −2.5008048 | 2.291004e−02 |
| as.factor(time)20 | 0.5393502 | 0.9437090 | 0.5715217 | 5.751253e−01 |
| gelhdf | −0.5903631 | 0.7753360 | −0.7614287 | 4.568346e−01 |
| gelpd | 4.1247611 | 0.8069953 | 5.1112577 | 8.687897e−05 |

Analysis of Variance Table

Response: PLAU

| | Df | Sum sq | Mean Sq | F value | Pr(>F) |
|---|---|---|---|---|---|
| as.factor(time) | 3 | 19.678 | 6.559 | 2.7279 | 0.07629. |
| gel | 2 | 95.166 | 47.583 | 19.7885 | 3.642e−05*** |
| Residuals | 17 | 40.878 | 2.405 | | |

---
Signif. codes:
0 '***'
0.001 '**'
0.01 '*'
0.05 '.'
0.1 ' ' 1

Ct-scale effects ...

| | Estimate | Std. Error | t value | Pr(>|t|) | DF | lower CI | upper CI |
|---|---|---|---|---|---|---|---|
| gel: pd v hdf | 4.7151241 | 0.8069953 | 5.8428147 | 1.957767e−05 | 17 | 3.012513 | 6.417735 |
| gel: pd v cd | 4.1247611 | 0.8069953 | 5.1112577 | 8.687897e−05 | 17 | 2.422150 | 5.827372 |
| gel: hdf v cd | −0.5903631 | 0.7753360 | −0.7614287 | 4.568346e−01 | 17 | −2.226179 | 1.045453 |

| | ratio scale (fold increases) ... | | |
|---|---|---|---|
| | Estimate | lower CI | upper CI |
| gel: pd/hdf | 26.2659916 | 8.069688 | 85.493063 |
| gel: pd/cd | 17.4452342 | 5.359691 | 56.782418 |
| gel: hdf/cd | 0.6641757 | 0.213724 | 2.064014 |

Pooled gel effects: $P = 3.642265e{-}05$
Pooled time effects: $P = 0.03556037$
Interaction: $P = 0.005705432$ -- VIM --
Pooled time effects model

| | Estimate | Std. Error | t value | Pr(>|t|) |
|---|---|---|---|---|
| (Intercept) | 30.0172891 | 0.4702316 | 63.8351203 | 1.092884e−21 |
| as.factor(time)4 | −0.9528084 | 0.5404802 | −1.7628923 | 9.588486e−02 |
| as.factor(time)13 | −0.6039229 | 0.5404802 | −1.1173821 | 2.793744e−01 |
| as.factor(time)20 | −0.2334739 | 0.5697161 | −0.4098074 | 6.870650e−01 |
| gelhdf | 0.9527619 | 0.4680696 | 2.0355134 | 5.769456e−02 |
| gelpd | 4.4913930 | 0.4871823 | 9.2191226 | 5.028666e−08 |

TABLE 7-continued

Analysis of Variance Table

Response: VIM

|  | Df | Sum Sq | Mean Sq | F value | Pr(>F) |
|---|---|---|---|---|---|
| as.factor(time) | 3 | 3.033 | 1.011 | 1.1536 | 0.3562 |
| gel | 2 | 81.009 | 40.504 | 46.2190 | 1.336e−07*** |
| Residuals | 17 | 14.898 | 0.876 | | |

---
Signif. codes:
0 '***'
0.001 '**'
0.01 '*'
0.05 '.'
0.1 ' ' 1

Ct-scale effects . . .

|  | Estimate | Std. Error | t value | Pr(>|t|) | DF | lower CI | upper CI |
|---|---|---|---|---|---|---|---|
| gel: pd v hdf | 3.538631 | 0.4871823 | 7.263465 | 1.324801e−06 | 17 | 2.51076636 | 4.566496 |
| gel: pd v cd | 4.491393 | 0.4871823 | 9.219123 | 5.028666e−08 | 17 | 3.46352827 | 5.519258 |
| gel: hdf v cd | 0.952762 | 0.4680696 | 2.035513 | 5.769456e−02 | 17 | −0.03477858 | 1.940302 | ratio scale (fold increases) . . .

|  | Estimate | lower CI | upper CI |
|---|---|---|---|
| gel: pd/hdf | 11.620748 | 5.6992274 | 23.694755 |
| gel: pd/cd | 22.492826 | 11.0312798 | 45.862965 |
| gel: hdf/cd | 1.935575 | 0.9761816 | 3.837861 |

Pooled gel effects: P = 1.336256e−07
Pooled time effects: P = 0.3466569
Interaction: P = 0.02552549

-- Col1a1 --
Pooled time effects model

|  | Estimate | Std. Error | t value | Pr(>|t|) |
|---|---|---|---|---|
| (Intercept) | 26.5039789 | 0.4713187 | 56.2336694 | 9.342400e−21 |
| as.factor(time)4 | −0.2469750 | 0.5417297 | −0.4559009 | 6.542311e−01 |
| as.factor(time)13 | −0.3855895 | 0.5417297 | −0.7117748 | 4.862580e−01 |
| as.factor(time)20 | 0.9806002 | 0.5710332 | 1.7172383 | 1.040967e−01 |
| gelhdf | 0.6490119 | 0.4691517 | 1.3833733 | 1.844492e−01 |
| gelpd | 1.1800736 | 0.4883086 | 2.4166555 | 2.719377e−02 |

Analysis of Variance Table

Response: Col1a1

|  | Df | Sum Sq | Mean Sq | F value | Pr(>F) |
|---|---|---|---|---|---|
| as.factor(time) | 3 | 4.9998 | 1.6666 | 1.8930 | 0.16910 |
| gel | 2 | 5.1984 | 2.5992 | 2.9523 | 0.07934. |
| Residuals | 17 | 14.9670 | 0.8804 | | |

---
Signif. codes:
0 '***'
0.001 '**'
0.01 '*'
0.05 '.'
0.1 ' ' 1

Ct-scale effects . . .

|  | Estimate | Std. Error | t value | Pr(>|t|) | DF | lower CI | upper CI |
|---|---|---|---|---|---|---|---|
| gel: pd v hdf | 0.5310616 | 0.4883086 | 1.087553 | 0.29197176 | 17 | −0.4991794 | 1.561303 |
| gel: pd v cd | 1.1800736 | 0.4883086 | 2.416655 | 0.02719377 | 17 | 0.1498326 | 2.210315 |
| gel: hdf v cd | 0.6490119 | 0.4691517 | 1.383373 | 0.18444923 | 17 | −0.3408116 | 1.638835 |

TABLE 7-continued

| | ratio scale (fold increases) . . . | | |
|---|---|---|---|
| | Estimate | lower CI | upper CI |
| gel: pd/hdf | 1.444992 | 0.7075091 | 2.951202 |
| gel: pd/cd | 2.265883 | 1.1094407 | 4.627762 |
| gel: hdf/cd | 1.568094 | 0.7895970 | 3.114144 |

Pooled gel effects: P = 0.07933785
Pooled time effects: P = 0.1199265
Interaction: P = 0.02199069

-- SMA --
Pooled time effects model

| | Estimate | Std. Error | t value | Pr(>|t|) |
|---|---|---|---|---|
| (Intercept) | 22.3822634 | 0.4782908 | 46.796350 | 1.509312e-18 |
| as.factor(time)4 | 0.6526979 | 0.5011473 | 1.302407 | 2.112136e-01 |
| as.factor(time)13 | 0.5049167 | 0.5011473 | 1.007522 | 3.286791e-01 |
| as.factor(time)20 | 1.0907642 | 0.5283292 | 2.064554 | 5.556774e-02 |
| gelhdf | 1.2631416 | 0.4285315 | 2.947605 | 9.457543e-03 |
| gelpd | 2.4145716 | 0.4465196 | 5.407537 | 5.809304e-05 |

Analysis of Variance Table

Response: SMA

| | Df | Sum Sq | Mean Sq | F value | Pr(>F) |
|---|---|---|---|---|---|
| as.factor(time) | 3 | 0.9940 | 0.3313 | 0.4888 | 0.6949218 |
| gel | 2 | 19.8383 | 9.9192 | 14.6324 | 0.0002437*** |
| Residuals | 16 | 10.8463 | 0.6779 | | |

---
Signif. codes:
0 '***'
0.001 '**'
0.01 '*'
0.05 '.'
0.1 ' ' 1

Ct-scale effects . . .

| | Estimate | Std. Error | t value | Pr(>|t|) | DF | lower CI | upper CI |
|---|---|---|---|---|---|---|---|
| gel: pd v hdf | 1.151430 | 0.4285315 | 2.686920 | 1.620001e-02 | 16 | 0.2429837 | 2.059876 |
| gel: pd v cd | 2.414572 | 0.4465196 | 5.407537 | 5.809304e-05 | 16 | 1.4679922 | 3.361151 |
| gel: hdf v cd | 1.263142 | 0.4285315 | 2.947605 | 9.457543e-03 | 16 | 0.3546953 | 2.171588 |

| | ratio scale (fold increases) . . . | | |
|---|---|---|---|
| | Estimate | lower CI | upper CI |
| gel: pd/hdf | 2.221340 | 1.183438 | 4.169505 |
| gel: pd/cd | 5.331611 | 2.766366 | 10.275601 |
| gel: hdf/cd | 2.400178 | 1.278715 | 4.505190 |

Pooled gel effects: P = 0.000243712
Pooled time effects: P = 0.2639338
Interaction: P = 0.02408090

-- PDGF --
Pooled time effects model

| | Estimate | Std. Error | t value | Pr(>|t|) |
|---|---|---|---|---|
| (Intercept) | 6.282407 | 2.061042 | 3.048170 | 0.018631174 |
| as.factor(time)4 | -7.534267 | 3.008299 | -2.504495 | 0.040723546 |
| as.factor(time)13 | -3.549044 | 2.468766 | -1.437578 | 0.193712454 |
| as.factor(time)20 | -4.002474 | 2.785143 | -1.437080 | 0.193848862 |
| gelhdf | 13.647218 | 2.882897 | 4.733855 | 0.002123001 |
| gelpd | 7.341584 | 2.468766 | 2.973787 | 0.020696303 |

TABLE 7-continued

Analysis of Variance Table

Response: PDGF

|  | Df | Sum Sq | Mean Sq | F value | Pr(>F) |
|---|---|---|---|---|---|
| as.factor(time) | 3 | 119.221 | 39.740 | 3.7099 | 0.069577. |
| gel | 2 | 242.417 | 121.209 | 11.3151 | 0.006409** |
| Residuals | 7 | 74.985 | 10.712 |  |  |

---

Signif. codes:
0 '***'
0.001 '**'
0.01 '*'
0.05 '.'
0.1 ' ' 1

Ct-scale effects . . .

|  | Estimate | Std. Error | t value | Pr(>|t|) | DF | lower CI | upper CI |
|---|---|---|---|---|---|---|---|
| gel: pd v hdf | −6.305634 | 2.578542 | −2.445426 | 0.044404102 | 7 | −12.402916 | −0.2083518 |
| gel: pd v cd | 7.341584 | 2.468766 | 2.973787 | 0.020696303 | 7 | 1.503881 | 13.1792875 |
| gel: hdf v cd | 13.647218 | 2.882897 | 4.733855 | 0.002123001 | 7 | 6.830249 | 20.4641869 | ratio scale (fold increases) . . .

|  | Estimate | lower CI | upper CI |
|---|---|---|---|
| gel: pd/hdf | 1.264198e−02 | 1.846504e−04 | 8.655255e−01 |
| gel: pd/cd | 1.621949e+02 | 2.836046e+00 | 9.276003e+03 |
| gel: hdf/cd | 1.282986e+04 | 1.137915e+02 | 1.446552e+06 |

Pooled gel effects: P = 0.00640867
Pooled time effects: P = 0.1571104
Interaction: P = 0.0009429007

-- Cox2 --
Pooled time effects model

|  | Estimate | Std. Error | t value | Pr(>|t|) |
|---|---|---|---|---|
| (Intercept) | 0.005703455 | 1.054733 | 0.005407486 | 9.957484e−01 |
| as.factor(time)4 | −0.172808384 | 1.212301 | −0.142545719 | 8.883248e−01 |
| as.factor(time)13 | 0.144410459 | 1.212301 | 0.119120914 | 9.065759e−01 |
| as.factor(time)20 | 3.092035363 | 1.277878 | 2.419664073 | 2.702842e−02 |
| gelhdf | 0.805886909 | 1.049884 | 0.767596240 | 4.532574e−01 |
| gelpd | 12.990524944 | 1.092754 | 11.887879259 | 1.161473e−09 |

Analysis of Variance Table

Response: Cox2

|  | Df | Sum Sq | Mean Sq | F value | Pr(>F) |
|---|---|---|---|---|---|
| as.factor(time) | 3 | 8.23 | 2.74 | 0.6221 | 0.6104 |
| gel | 2 | 763.14 | 381.57 | 86.5435 | 1.224e−09*** |
| Residuals | 17 | 74.95 | 4.41 |  |  |

---

Signif. codes:
0 '***'
0.001 '**'
0.01 '*'
0.05 '.'
0.1 ' ' 1

Ct-scale effects . . .

|  | Estimate | Std. Error | t value | Pr(>|t|) | DF | lower CI | upper CI |
|---|---|---|---|---|---|---|---|
| gel: pdvhdf | 12.1846380 | 1.092754 | 11.1503966 | 3.068126e−09 | 17 | 9.879129 | 14.490147 |
| gel: pdvcd | 12.9905249 | 1.092754 | 11.8878793 | 1.161473e−09 | 17 | 10.685016 | 15.296034 |
| gel: hdfvcd | 0.8058869 | 1.049884 | 0.7675962 | 4.532574e−01 | 17 | −1.409174 | 3.020948 |

TABLE 7-continued ratio scale (fold increases) . . .

|  | Estimate | lower CI | upper CI |
|---|---|---|---|
| gel: pd/hdf | 4655.234201 | 941.7035099 | 23012.76914 |
| gel: pd/cd | 8138.374442 | 1646.3050936 | 40231.38774 |
| gel: hdf/cd | 1.748220 | 0.3765271 | 8.11701 |

Pooled gel effects:   P = 1.223833e−09
Pooled time effects:  P = 0.0696079
Interaction:          P = 0.7099217

-- GAPDH --
Pooled time effects model

|  | Estimate | Std. Error | t value | Pr(>|t|) |
|---|---|---|---|---|
| (Intercept) | 30.0742220 | 0.4569035 | 65.8218227 | 6.503757e−22 |
| as.factor(time)4 | −0.3744750 | 0.5251610 | −0.7130671 | 4.854782e−01 |
| as.factor(time)13 | −0.8255895 | 0.5251610 | −1.5720693 | 1.343598e−01 |
| as.factor(time)20 | −1.1853720 | 0.5535683 | −2.1413292 | 4.702891e−02 |
| gelhdf | −1.5791131 | 0.4548028 | −3.4720831 | 2.915224e−03 |
| gelpd | −0.1450306 | 0.4733738 | −0.3063765 | 7.630385e−01 |

Analysis of Variance Table

Response: GAPDH

|  | Df | Sum Sq | Mean Sq | F value | Pr(>F) |
|---|---|---|---|---|---|
| as.factor(time) | 3 | 5.0212 | 1.6737 | 2.0229 | 0.148867 |
| gel | 2 | 11.9684 | 5.9842 | 7.2327 | 0.005336** |
| Residuals | 17 | 14.0655 | 0.8274 |  |  |

---
Signif. codes:
0 '***'
0.001 '**'
0.01 '*'
0.05 '.'
0.1 ' ' 1

Ct-scale effects . . .

|  | Estimate | Std. Error | t value | Pr(>|t|) | DF | lower CI | upper CI |
|---|---|---|---|---|---|---|---|
| gel: pdvhdf | 1.4340825 | 0.4733738 | 3.0294930 | 0.007563439 | 17 | 0.4353512 | 2.4328138 |
| gel: pdvcd | −0.1450306 | 0.4733738 | −0.3063765 | 0.763038514 | 17 | −1.1437619 | 0.8537007 |
| gel: hdfvcd | −1.5791131 | 0.4548028 | −3.4720831 | 0.002915224 | 17 | −2.5386631 | −0.6195631 | ratio scale (fold increases) . . .

|  | Estimate | lower CI | upper CI |
|---|---|---|---|
| gel: pd/hdf | 2.7021026 | 1.3522399 | 5.399455 |
| gel: pd/cd | 0.9043602 | 0.4525779 | 1.807131 |
| gel: hdf/cd | 0.3346876 | 0.1721021 | 0.650868 |

Pooled gel effects:   P = 0.005336279
Pooled time effects:  P = 0.1882468
Interaction:          P = 0.1006312

From Table 7 it can be seen that:

Col16a: pd induces significantly more RNA activity than either control by 2.8 and 3.8-fold. There is no evidence for a time-effect.

APOD: pd induces significantly more RNA activity than either control by 4.3 and 7.5-fold. There are strong time-effects, and evidence that these differ between gels. The pd seems to have a steeper induction with time, whilst hdf has an early peak (artefact). The non-interaction model is nonetheless a good summary of the overall behaviour.

MMP2: pd significantly exceeds cd (2-fold) but not hdf. There is some evidence for an interaction. However fit is strongly influenced by one outlier at 20 d/pd.

INSIG1: pd significantly exceeds cd (2.4-fold) but not hdf. Formally the interaction is significant, but the non-interaction model is a good summary.

Col13a1: Massive induction compared to both controls (12 and 76-fold). No evidence of time effects.

RPL32: pd increased relative to both controls.

Gas6: pd increased relative to cd (2.2-fold) but not significantly relative to hdf (1.7-fold). Quite strong evidence of interaction with pd showing steeper rise with time and hdf and cd a fall with time. In fact pd is less than hdf at zero time. The non-interaction model is not very good here as the magnitude and sign of the effect depend on the chosen time scale. But the significance of the interaction demonstrate what is going on quite effectively.

PAI: pd induces significantly more RNA activity than either control by 2.6 d 3.3 fold. Very strong time effects. There is a significant interaction, but the non-interaction model looks a good summary—maybe the hdf and pd go up at the last time point and the cd stays level or goes down, but the data are very scattered.

PLAU: Massive induction compared to both controls (26 and 17-fold). No evidence of time effects. Significant interaction, but not very interpretable.

VIM: Massive induction compared to both controls (12 and 22-fold). No evidence of time effects. Some quite scattered data. Significant interaction, but not very interpretable—pd high at end Coll1a1: pd higher than cd (2.3-fold) but not hdf. Significant interaction but largely due to abnormally (?) high final value in pd.

SMA: pd induces significantly more RNA activity than either control by 2.2 d 5.3 fold. Significant interaction but maybe due to abnormally (?) high final value in pd. hdf is decreasing with time whilst the other two are increasing, but difficult to draw real conclusions. One abnormally (?) low value in hdf/20 d—this may be an outlier.

PDGF: pd is significantly higher than cd (1.6-fold) but significantly lower than hdf (79-fold).

Cox2: Massive induction compared to both controls (5000 and 8000-fold). No significant time effects. One outlier (hdf/20 d).

GAPDH: pd significantly higher than hdf (2.7-fold) but not cd. A general decrease with time is not significant (might be if we did a trend test) two outliers (hdf/20 d, pd/20 d)

To summarise:

The following genes, when expressed by fibroblasts in a fibrin matrix, showed a statistically significantly greater than two-fold increase in expression compared to cells cultured in a collagen matrix or when cultured alone. Collagen 6a1 (Coll6a), Apolipoprotein D (APOD), Collagen 3a1 (Coll3a1), Ribosomal protein L32 (RPL32), Plasminogen activator inhibitor (PAI), urinary plasminogen activator (PLAU), Vimentin (Vim), Smooth muscle actin (SMA) and cyclo-oxygenase 2 (Cox2).

The following genes showed a statistically significant increase in expression in fibroblasts in a fibrin matrix compared to cells cultured in a collagen matrix. Matrix metalloprotease 2 (MMP2), Insulin induced gene 1 (INSIG1), Growth arrest specific gene 6 (Gas6) and Collagen 1a1 (Coll1a).

Glyeraldehyde-3-phosphate dehydrogenase (GAPDH) showed a statistically significant increase in expression in a fibrin matrix compared to cells cultured alone.

Time is a factor that determines the level of expression in the following genes: Apolipoprotein D ($p<0.0001$), Matrix metalloproteinase 2, ($p<0.05$), Ribosomal protein L32 ($p<0.05$), Plasminogen activator inhibitor ($p<0.0001$) and urinary plasminogen activator ($p<0.05$).

The foregoing examples are meant to illustrate the invention and do not limit it in any way. One of skill in the art will recognise modifications within the spirit and scope of the invention as indicated in the claims.

All references cited herein are hereby incorporated by reference.

The invention claimed is:

1. A wound healing composition comprising isolated living dermal fibroblast cells having a wound healing phenotype, characterized in that:

(i) the cells of the composition exhibit, at less than 14 days, a 2.08 to 48,200-fold higher level of expression of apolipoprotein D (ApoD); a 694 to 662,000-fold higher level of expression of matrix metalloprotease 2 (MMP2); a 33.7 to 43,300-fold higher level of expression of collagen 3a1 (Coll3a1); and a 20.2 to 121,000-fold higher level of expression of smooth muscle actin (SMA) relative to the expression level of Ribosomal protein L32 (RPL32); or (ii) 75-99% of the cells of the composition have a banding pattern of polymerase chain reaction (PCR) products resulting from differential display identical or similar to that shown in FIG. 4 or FIG. 5 for nucleic acid expression in fibrin, wherein the dermal fibroblast cells are comprised within a fibrin support matrix formed by thrombin-mediated polymerization of a fibrinogen and said dermal fibroblasts followed by incubation of said fibrin support matrix at about 37° C. for about 16-24 hours after formation of said matrix, and wherein said composition has a shelf-life of at least 7 and up to 28 days, when stored at about 2° to 8° C.

2. The wound healing composition of claim 1, in which the matrix is non-pyrogenic and/or sterile.

3. The wound healing composition of claim 1, in which the matrix is solid or semi-solid.

4. The wound healing composition of claim 1, in which the cells are mammalian.

5. The wound healing composition of claim 1, in which the cells substantially exclude keratinocytes.

6. The wound healing composition of claim 1, in which the cells exhibit, at less than 14 days, a 360-fold higher mean level of expression of ApoD; a 102,000-fold higher mean level of expression of MMP2; a 800 to 4370-fold higher mean level of expression of Coll3a1; or a 14,100-fold mean higher level of expression of SMA relative to the level of expression of RPL32.

7. The wound healing composition of claim 1, in which the cells are suspended substantially uniformly within the matrix.

8. The wound healing composition of claim 1, in which the matrix has a protein concentration in the range of about 3 to 12 mg.ml$^{-1}$.

9. The wound healing composition of claim 1, in which the cells are human.

10. The wound healing composition of claim 1, in which fibroblasts comprise between about 90% to 100% of the cells of said composition.

11. The wound healing composition of claim 1, in which the cells are not proliferating or not senescent.

12. The wound healing composition of claim 1, further comprising a protease inhibitor.

13. The wound healing composition of claim 12, in which the protease inhibitor is aprotinin or tranexamic acid.

14. The wound healing composition of claim 1, in which the composition has a thickness of approximately 8 mm or less.

15. The wound healing composition of claim 14, in which the composition has a thickness of approximately 5 mm or less.

16. The wound healing composition of claim 1, comprising about 450 to 2500 cells per mm$^2$.

17. The wound healing composition of claim 1, in which the composition is single-layered.

18. The wound healing composition of claim 1, in which the composition is packaged in a container suitable for transporting the composition, storing the composition, or topically applying the composition to a skin surface.

19. The wound healing composition of claim 18, in which the container comprises a flexible pouch consisting of two sheets of impermeable flexible material peripherally sealed to provide a means of containment for the composition, the pouch comprising a first internal surface to which the composition is adherent at a level of adhesion more than between the composition and a second internal surface of the pouch but less than that between the composition and the skin surface, such that in use the pouch may be opened by parting the sheets and the composition conveniently manipulated and directly applied to the skin surface without further requirement for the composition to be touched directly by any other means prior to application.

20. The wound healing composition of claim 1, wherein said wound healing composition is a topical composition.

21. The wound healing composition of claim 1, wherein 90-99% of the cells of the composition have a banding pattern of polymerase chain reaction (PCR) products resulting from differential display identical or similar to that shown in FIG. 4 or FIG. 5 for nucleic acid expression in fibrin.

* * * * *

UNITED STATES PATENT AND TRADEMARK OFFICE
CERTIFICATE OF CORRECTION

| | | |
|---|---|---|
| PATENT NO. | : 8,765,169 B2 | Page 1 of 1 |
| APPLICATION NO. | : 10/589150 | |
| DATED | : July 1, 2014 | |
| INVENTOR(S) | : Kemp et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1688 days.

Signed and Sealed this
Twenty-fourth Day of November, 2015

Michelle K. Lee
*Director of the United States Patent and Trademark Office*

```
                        SEQUENCE LISTING

<160> NUMBER OF SEQ ID NOS: 47

<210> SEQ ID NO 1
<211> LENGTH: 40
<212> TYPE: DNA
<213> ORGANISM: Artificial Sequence
<220> FEATURE:
<223> OTHER INFORMATION: synthetic

<400> SEQUENCE: 1
catctcgagc ggccgctttt tttttttttt tttttttttt                              40

<210> SEQ ID NO 2
<211> LENGTH: 21
<212> TYPE: DNA
<213> ORGANISM: Artificial Sequence
<220> FEATURE:
<223> OTHER INFORMATION: synthetic

<400> SEQUENCE: 2
ggtaacaggg tagggcatgg t                                                  21

<210> SEQ ID NO 3
<211> LENGTH: 17
<212> TYPE: DNA
<213> ORGANISM: Artificial Sequence
<220> FEATURE:
<223> OTHER INFORMATION: synthetic

<400> SEQUENCE: 3 ccacccccccc ccataaa                                                      17

<210> SEQ ID NO 4
<211> LENGTH: 16
```

```
<212> TYPE: DNA
<213> ORGANISM: Artificial Sequence
<220> FEATURE:
<223> OTHER INFORMATION: synthetic

<400> SEQUENCE: 4
gggctgagcg ggaagc                                                        16

<210> SEQ ID NO 5
<211> LENGTH: 25
<212> TYPE: DNA
<213> ORGANISM: Artificial Sequence
<220> FEATURE:
<223> OTHER INFORMATION: synthetic

<400> SEQUENCE: 5
cccctgttca ctctacttag catgt                                              25

<210> SEQ ID NO 6
<211> LENGTH: 24
<212> TYPE: DNA
<213> ORGANISM: Artificial Sequence
<220> FEATURE:
<223> OTHER INFORMATION: synthetic

<400> SEQUENCE: 6
cattagcacc ataacatgcg tctt                                               24

<210> SEQ ID NO 7
<211> LENGTH: 23
<212> TYPE: DNA
<213> ORGANISM: Artificial Sequence
<220> FEATURE:
<223> OTHER INFORMATION: synthetic

<400> SEQUENCE: 7
ggtgctcctc tttttcttg tca                                                 23

<210> SEQ ID NO 8
<211> LENGTH: 16
<212> TYPE: DNA
<213> ORGANISM: Artificial Sequence
<220> FEATURE:
<223> OTHER INFORMATION: synthetic

<400> SEQUENCE: 8
gggcccacgg ctgagt                                                        16

<210> SEQ ID NO 9
<211> LENGTH: 29
<212> TYPE: DNA
<213> ORGANISM: Artificial Sequence
<220> FEATURE:
<223> OTHER INFORMATION: synthetic

<400> SEQUENCE: 9
ggcctgtaac atatctgtaa atagtgaga                                          29

<210> SEQ ID NO 10
<211> LENGTH: 21
<212> TYPE: DNA
<213> ORGANISM: Artificial Sequence
<220> FEATURE:
<223> OTHER INFORMATION: synthetic

<400> SEQUENCE: 10
```

-continued gcactcaagg gcaaggatat g                                              21

<210> SEQ ID NO 11
<211> LENGTH: 18
<212> TYPE: DNA
<213> ORGANISM: Artificial Sequence
<220> FEATURE:
<223> OTHER INFORMATION: synthetic

<400> SEQUENCE: 11
gcgtgcccag ctcttcac                                                  18

<210> SEQ ID NO 12
<211> LENGTH: 23
<212> TYPE: DNA
<213> ORGANISM: Artificial Sequence
<220> FEATURE:
<223> OTHER INFORMATION: synthetic

<400> SEQUENCE: 12
aaactgagac agtgctggtc aca                                            23

<210> SEQ ID NO 13
<211> LENGTH: 17
<212> TYPE: DNA
<213> ORGANISM: Artificial Sequence
<220> FEATURE:
<223> OTHER INFORMATION: synthetic

<400> SEQUENCE: 13 gggtcccca cgtgaca                                                    17

<210> SEQ ID NO 14
<211> LENGTH: 26
<212> TYPE: DNA
<213> ORGANISM: Artificial Sequence
<220> FEATURE:
<223> OTHER INFORMATION: synthetic

<400> SEQUENCE: 14
ttgtaggagt gtcggttgtt aagaac                                         26

<210> SEQ ID NO 15
<211> LENGTH: 23
<212> TYPE: DNA
<213> ORGANISM: Artificial Sequence
<220> FEATURE:
<223> OTHER INFORMATION: synthetic

<400> SEQUENCE: 15
tcaagtgcct ttctgcagtt ttt                                            23

<210> SEQ ID NO 16
<211> LENGTH: 18
<212> TYPE: DNA
<213> ORGANISM: Artificial Sequence
<220> FEATURE:
<223> OTHER INFORMATION: synthetic

<400> SEQUENCE: 16
ggcccggctt catcgtat                                                  18

<210> SEQ ID NO 17
<211> LENGTH: 18
<212> TYPE: DNA
<213> ORGANISM: Artificial Sequence

```
<220> FEATURE:
<223> OTHER INFORMATION: synthetic

<400> SEQUENCE: 17
ggctccatcc tggcctct                                                    18

<210> SEQ ID NO 18
<211> LENGTH: 24
<212> TYPE: DNA
<213> ORGANISM: Artificial Sequence
<220> FEATURE:
<223> OTHER INFORMATION: synthetic

<400> SEQUENCE: 18
ccccaaaaat ataatcaccg actt                                             24

<210> SEQ ID NO 19
<211> LENGTH: 21
<212> TYPE: DNA
<213> ORGANISM: Artificial Sequence
<220> FEATURE:
<223> OTHER INFORMATION: synthetic

<400> SEQUENCE: 19
cacctccctt cccacctact g                                                21

<210> SEQ ID NO 20
<211> LENGTH: 26
<212> TYPE: DNA
<213> ORGANISM: Artificial Sequence
<220> FEATURE:
<223> OTHER INFORMATION: synthetic

<400> SEQUENCE: 20
aaacgaagtg tttgagaaga ctgtgt                                           26

<210> SEQ ID NO 21
<211> LENGTH: 24
<212> TYPE: DNA
<213> ORGANISM: Artificial Sequence
<220> FEATURE:
<223> OTHER INFORMATION: synthetic

<400> SEQUENCE: 21
aattcagtag gtgcattgga atca                                             24

<210> SEQ ID NO 22
<211> LENGTH: 20
<212> TYPE: DNA
<213> ORGANISM: Artificial Sequence
<220> FEATURE:
<223> OTHER INFORMATION: synthetic

<400> SEQUENCE: 22
acactcagac ccccaccaca                                                  20

<210> SEQ ID NO 23
<211> LENGTH: 19
<212> TYPE: DNA
<213> ORGANISM: Artificial Sequence
<220> FEATURE:
<223> OTHER INFORMATION: synthetic

<400> SEQUENCE: 23
cataggcccc tcccctctt                                                   19
```

```
<210> SEQ ID NO 24
<211> LENGTH: 20
<212> TYPE: DNA
<213> ORGANISM: Artificial Sequence
<220> FEATURE:
<223> OTHER INFORMATION: synthetic

<400> SEQUENCE: 24
ctggccatca gagtcaccaa                                               20

<210> SEQ ID NO 25
<211> LENGTH: 24
<212> TYPE: DNA
<213> ORGANISM: Artificial Sequence
<220> FEATURE:
<223> OTHER INFORMATION: synthetic

<400> SEQUENCE: 25
tgagctgcct actcattttc ttca                                          24

<210> SEQ ID NO 26
<211> LENGTH: 22
<212> TYPE: DNA
<213> ORGANISM: Artificial Sequence
<220> FEATURE:
<223> OTHER INFORMATION: synthetic

<400> SEQUENCE: 26
caccgttaat ctcgagggtc tt                                            22

<210> SEQ ID NO 27
<211> LENGTH: 22
<212> TYPE: DNA
<213> ORGANISM: Artificial Sequence
<220> FEATURE:
<223> OTHER INFORMATION: synthetic

<400> SEQUENCE: 27
tgaccccgac ctcagagagt ac                                            22

<210> SEQ ID NO 28
<211> LENGTH: 25
<212> TYPE: DNA
<213> ORGANISM: Artificial Sequence
<220> FEATURE:
<223> OTHER INFORMATION: synthetic

<400> SEQUENCE: 28
aatgaaatcg aatacttggg aagct                                         25

<210> SEQ ID NO 29
<211> LENGTH: 20
<212> TYPE: DNA
<213> ORGANISM: Artificial Sequence
<220> FEATURE:
<223> OTHER INFORMATION: synthetic

<400> SEQUENCE: 29
tctgtgccct ggagcattct                                               20

<210> SEQ ID NO 30
<211> LENGTH: 22
<212> TYPE: DNA
<213> ORGANISM: Artificial Sequence
<220> FEATURE:
<223> OTHER INFORMATION: synthetic
```

```
<400> SEQUENCE: 30
ggatggaggg agtttacagg aa                                              22

<210> SEQ ID NO 31
<211> LENGTH: 19
<212> TYPE: DNA
<213> ORGANISM: Artificial Sequence
<220> FEATURE:
<223> OTHER INFORMATION: synthetic

<400> SEQUENCE: 31
gtgccccaga ccaggaatt                                                  19

<210> SEQ ID NO 32
<211> LENGTH: 20
<212> TYPE: DNA
<213> ORGANISM: Artificial Sequence
<220> FEATURE:
<223> OTHER INFORMATION: synthetic

<400> SEQUENCE: 32
tccctgtgcc cagagtaacc                                                 20

<210> SEQ ID NO 33
<211> LENGTH: 23
<212> TYPE: DNA
<213> ORGANISM: Artificial Sequence
<220> FEATURE:
<223> OTHER INFORMATION: synthetic

<400> SEQUENCE: 33
aggtctggct cctgtgtttt aca                                             23

<210> SEQ ID NO 34
<211> LENGTH: 25
<212> TYPE: DNA
<213> ORGANISM: Artificial Sequence
<220> FEATURE:
<223> OTHER INFORMATION: synthetic

<400> SEQUENCE: 34
ttattgaaag ctgacctgct aatga                                           25

<210> SEQ ID NO 35
<211> LENGTH: 20
<212> TYPE: DNA
<213> ORGANISM: Artificial Sequence
<220> FEATURE:
<223> OTHER INFORMATION: synthetic

<400> SEQUENCE: 35
gggcagtcac ccattcaatt                                                 20

<210> SEQ ID NO 36
<211> LENGTH: 22
<212> TYPE: DNA
<213> ORGANISM: Artificial Sequence
<220> FEATURE:
<223> OTHER INFORMATION: synthetic

<400> SEQUENCE: 36
cccatagagc tggtgaggaa gt                                              22

<210> SEQ ID NO 37
```

```
<211> LENGTH: 17
<212> TYPE: DNA
<213> ORGANISM: Artificial Sequence
<220> FEATURE:
<223> OTHER INFORMATION: synthetic

<400> SEQUENCE: 37
cgttcgtccc cgatgga                                                    17

<210> SEQ ID NO 38
<211> LENGTH: 19
<212> TYPE: DNA
<213> ORGANISM: Artificial Sequence
<220> FEATURE:
<223> OTHER INFORMATION: synthetic

<400> SEQUENCE: 38
gtccacagtg ccccttcct                                                  19

<210> SEQ ID NO 39
<211> LENGTH: 17
<212> TYPE: DNA
<213> ORGANISM: Artificial Sequence
<220> FEATURE:
<223> OTHER INFORMATION: synthetic

<400> SEQUENCE: 39
cgctccctgg catcatg                                                    17

<210> SEQ ID NO 40
<211> LENGTH: 19
<212> TYPE: DNA
<213> ORGANISM: Artificial Sequence
<220> FEATURE:
<223> OTHER INFORMATION: synthetic

<400> SEQUENCE: 40
aagcgatgca cgcaagaag                                                  19

<210> SEQ ID NO 41
<211> LENGTH: 23
<212> TYPE: DNA
<213> ORGANISM: Artificial Sequence
<220> FEATURE:
<223> OTHER INFORMATION: synthetic

<400> SEQUENCE: 41
aagaatgcca aaatcagcag tct                                             23

<210> SEQ ID NO 42
<211> LENGTH: 20
<212> TYPE: DNA
<213> ORGANISM: Artificial Sequence
<220> FEATURE:
<223> OTHER INFORMATION: synthetic

<400> SEQUENCE: 42
ggcaataagc gcctctacca                                                 20

<210> SEQ ID NO 43
<211> LENGTH: 19
<212> TYPE: DNA
<213> ORGANISM: Artificial Sequence
<220> FEATURE:
<223> OTHER INFORMATION: synthetic

<400> SEQUENCE: 43
```

```
cctcgagcag cagcagaac                                                      19

<210> SEQ ID NO 44
<211> LENGTH: 20
<212> TYPE: DNA
<213> ORGANISM: Artificial Sequence
<220> FEATURE:
<223> OTHER INFORMATION: synthetic

<400> SEQUENCE: 44
tcagggcaac accacacact                                                     20

<210> SEQ ID NO 45
<211> LENGTH: 23
<212> TYPE: DNA
<213> ORGANISM: Artificial Sequence
<220> FEATURE:
<223> OTHER INFORMATION: synthetic

<400> SEQUENCE: 45
ccatgtttga gcttctgttt caa                                                 23

<210> SEQ ID NO 46
<211> LENGTH: 20
<212> TYPE: DNA
<213> ORGANISM: Artificial Sequence
<220> FEATURE:
<223> OTHER INFORMATION: synthetic

<400> SEQUENCE: 46
tcatgccaaa gccagttgtc                                                     20

<210> SEQ ID NO 47
<211> LENGTH: 24
<212> TYPE: DNA
<213> ORGANISM: Artificial Sequence
<220> FEATURE:
<223> OTHER INFORMATION: synthetic

<400> SEQUENCE: 47
cacaccggat gtcatctttg tatt                                                24
```